(12) United States Patent
Dantzig et al.

(10) Patent No.: US 7,038,077 B2
(45) Date of Patent: May 2, 2006

(54) PRODRUGS OF EXCITATORY AMINO ACIDS

(75) Inventors: Anne Hollins Dantzig, Crawfordsville, IN (US); James Allen Monn, Indianapolis, IN (US); Stephanie Ann Sweetana, Carmel, IN (US); Ana Belen Bueno Melendo, Madrid (ES); Alfonso De Dios, Madrid (ES); Carmen Dominguez-Fernandez, Madrid (ES); Marc Francis Herin, Perwez (BE); Luisa Maria Martin-Cabrejas, Madrid (ES); Jose Alfredo Martin, Madrid (ES); Maria Angeles Martinez-Grau, Madrid (ES); Carlos Montero Salgado, Madrid (ES); Concepcion Pedregal-Tercero, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 198 days.

(21) Appl. No.: 10/465,972

(22) PCT Filed: Jan. 9, 2002

(86) PCT No.: PCT/US02/00488

§ 371 (c)(1),
(2), (4) Date: Jan. 26, 2004

(87) PCT Pub. No.: WO02/055485

PCT Pub. Date: Jul. 18, 2002

(65) Prior Publication Data

US 2004/0138304 A1   Jul. 15, 2004

Related U.S. Application Data

(60) Provisional application No. 60/361,644, filed on Oct. 22, 2001, provisional application No. 60/329,789, filed on Oct. 16, 2001.

(30) Foreign Application Priority Data

Jan. 11, 2001 (EP) ................................. 01500008
Aug. 2, 2001 (EP) ................................. 01500208
Nov. 7, 2001 (EP) ................................. 01500264

(51) Int. Cl.
 *C07C 61/12* (2006.01)
(52) U.S. Cl. ...................... 562/501; 562/502
(58) Field of Classification Search ................ 514/561; 562/501, 502
See application file for complete search history.

(56) References Cited

U.S. PATENT DOCUMENTS

| | | | |
|---|---|---|---|
| 5,661,184 A | 8/1997 | Helton et al. | |
| 5,726,320 A | 3/1998 | Robey | |
| 5,750,566 A | 5/1998 | Schoepp et al. | |
| 5,882,671 A | 3/1999 | Helton et al. | |
| 5,912,248 A * | 6/1999 | Fernandez et al. | 514/256 |
| 5,925,680 A | 7/1999 | Helton et al. | |
| 5,925,782 A | 7/1999 | Monn | |
| 5,958,960 A * | 9/1999 | Massey et al. | 514/393 |

FOREIGN PATENT DOCUMENTS

| | | |
|---|---|---|
| EP | 0 696 577 A | 2/1996 |
| EP | 1 052 246 A | 11/2000 |
| WO | WO 00 04010 A | 1/2000 |
| WO | WO 02 22627 A | 3/2002 |
| WO | WO 02/055485 A1 | 7/2002 |
| WO | WO 03/006489 A2 | 1/2003 |

OTHER PUBLICATIONS

PCT/US02/36145, pending, Bueno Melando et al.
C. Y. Yang et al., Intestinal peptide transport systems and oral drug availability, *Pharm. Res.* 1999, 16(9), 1331-1343.
V. Ganapathy et al., Intestinal transport of amino acids and peptides, *Physiology of the gastrointestinal tract*, L. R. Johnson, Editor. 1994, Raven Press: New York, pp. 1773-1794.
D. M. Mathews et al., Peptide absorption, *Gastroenterology* 1976, 71, 151-161.
K. Inui, M. et al., Transepithelial transport of oral cephalosporins by monolayers of intestinal epithelial cell line Caco-2: Specific transport systems in apical and basolateral membranes, *J. Pharmacol. Exp. Ther*, 1992, 261(1), 195-201.
Kim, J. S. et al., Absorption of ACE inhibitors from small intestine and colon, *J. Pharm. Sci.* 1994, 83(9), 1350-1356.
Hashimoto, N. et al., Renin inhibitor: transport mechanism in rat small intestinal brush-border membrane vesicles, *Pharm. Res.* 1994, 11(10), 1448-1451.

(Continued)

*Primary Examiner*—Johann Richter
*Assistant Examiner*—Chukwuma Nwaonicha
(74) *Attorney, Agent, or Firm*—Arvie J. Anderson; Mark A. Winter

(57) ABSTRACT

This invention relates to synthetic excitatory amino acid prodrugs and processes for their preparation. The invention further relates to methods of using, and pharmaceutical compositions comprising, the compounds for the treatment of neurological disorders and psychiatric disorders.

12 Claims, No Drawings

OTHER PUBLICATIONS

Döring, F. et al., Minimal molecular determinants of substrates for recognition by the intestinal peptide transporter, *J. Biol. Chem.* 1998, 273, 23211-23218.

Han, H. K. et al., 5'-Amino acid esters of antiviral nucleosides, acyclovir, and AZT are absorbed by the intestinal PEPT1 peptide transporter, *Pharm. Res.* 1998, 15, 1154-1159.

Hu, M. et al, Use of peptide carrier system to improve the intestinal absorption of L-alpha-methyldopa: carrier kinetics, intestinal permeabilities and in vitro hydrolysis of dipeptidyl derivatives of L-alpha-methyldopa. *Pharm Res.* 1989, 6, 66-70.

Bailey, P. D. et al., How to make drugs orally active: a substrate template for peptide transporter PepT1, *Angew. Chem. Int. Ed. Eng.* 2000, 39(3), 506-508.

Bai, Jane P. F. et al, Structural Specificity of Mucosal-Cell Transport and Metabolism of Peptide Drugs: Implication for Oral Peptide Drug Delivery., *Pharm. Res.*, 9 (8), 1992, 969-978.

Langguth P. et al., The challenge of proteolytic enzymes in intestinal peptide delivery., *Journal of Controlled Release*, 46, 1997, 39-57.

Walter E. et al., The intestinal peptide carrier: A potential transport system for small peptide derived drugs, *Adv. Drug. Deliv. Rev.* 1996, 20, 33-58.

Amidon G. L. et al., Absorption of Peptide and Peptidomimetic drugs., *Annu. Rev. Pharmacol. Toxicol.*, 1994, 34, 321-341.

Bai, Jane P-F et al., Utiliization of Peptide Carrier System To Improve Intestinal Absorption: Targeting Prolidase as a Prodrug-Converting Enzyme., *J. Pharm. Sci.*, 1992, 81 (2), 113-116.

Lee, Chao-Pin et al., Advanced Drug Delivery, 23, 1997, 47-62.

Pauletti, Giovanni M. et al., Advanced Drug Delivery Reviews, 1997, 27, 235-256.

Oliyai, Reza, Advanced Drug Delivery Reviews, 1996, 19, 275-286.

Steffansen, Bente et al., European Journal of Pharmaceutical Sciences, 1999, 8, 67-73.

Nielsen, Carsten Uhd et al., Journal of Controlled Release, 2001, 76, 129-138.

Steingrimsdottir, Hlif et al., Antimicrobial Agents and Chemotherapy, 2000, 44 (1), 207-9.

Anand, Banmeet S. et al., Current prodrug strategies via membrane transporters/receptors, Expert Opin. Biol. Ther., 2002, 2(6), 607-620.

Dantzig, Anne H., Oral absorption of β-lactams by intestinal peptide transport proteins, Advanced Drug Delivery Reviews, 1997, 63-76.

\* cited by examiner

PRODRUGS OF EXCITATORY AMINO ACIDS

This is the national phase application under 35 USC 371 for PCT/US02/00488, filed Jan. 9, 2002, which claims the benefit of European Application No. 01500264.5, filed Nov. 7, 2001, U.S. Provisional Application No. 60/361,444, filed Oct. 22, 2001, U.S. Provisional Application No. 60/329,789, filed Oct. 16, 2001, European Application No. 01500208.2 filed Aug. 7, 2001 and European Application No. 01500008.6 filed Jan. 11, 2001.

This invention relates to synthetic excitatory amino acid prodrugs (and their pharmaceutically acceptable salts) and processes for their preparation. The invention further relates to methods of using, and pharmaceutical compositions comprising, the compounds for the treatment of neurological disorders and psychiatric disorders.

Treatment of neurological or psychiatric disorders, such as anxiety disorder, have been linked to selective activation of metabotropic excitatory amino acid receptors such as (+)-2-aminobicyclo[3.1.0]hexane-2,6-dicarboxylic acid, also known as LY354740, which is disclosed in U.S. Pat. No. 5,750,566 (the '566 patent) issued May 12, 1998 is an mGlu2 receptor agonist. CNS Drug Reviews, 5, pgs. 1–12 (1999).

The present invention provides for a prodrug form of LY354740 which enhances the oral exposure of LY354740. The present invention also provides for prodrug forms of other compounds which possess improved oral exposure. Compounds of the present invention represent an improved approach for maintaining LY354740-like safety and efficacy in humans with increased oral bioavailability. Preclinical studies with compounds of the present invention, has shown greatly enhanced oral exposure of the parent compound.

Accordingly, the present invention provides a compound of the formula I

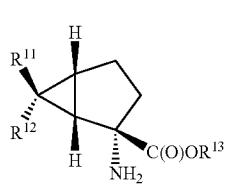

wherein
$R^{11}$ is $C(O)OR^{14}$ and $R^{12}$ is hydrogen or fluoro; or $R^{11}$ is hydrogen or fluoro and $R^{12}$ is $C(O)OR^{14}$; and
$R^{13}$ and $R^{14}$ are, independently, hydrogen, (1–6C) heterocyclylalkyl, aryl or (1–6C) arylalkyl;
provided when $R^{13}$ is hydrogen, $R^{14}$ is not hydrogen;
or a pharmaceutically acceptable salt thereof.

Compounds of the invention have been found to be useful prodrugs for selective agonists of metabotropic glutamate receptors and are therefore useful in the treatment of diseases of the central nervous system such as neurological diseases, for example neurodegenerative diseases, and as antipsychotic, anxiolytic, drug-withdrawal, antidepressant, anticonvulsant, analgesic and anti-emetic agents.

It will be appreciated that the compounds of formula (I) contain at least four asymmetric carbon atoms, three being in the cyclopropane ring and one being at the α-carbon of the amino acid group. Additional asymmetric carbons may be present in the generic radicals as defined. Accordingly, the compounds of the present invention may exist in and be isolated in enantiomerically pure form, in racemic form, or in a diastereoisomeric mixture.

The amino acid moiety within the cyclopentane ring preferably has the natural amino acid configuration, i.e. the L-configuration relating to D-glyceraldehyde.

The present invention includes pharmaceutically acceptable salts of the compound of formula I. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I. The alkali metal and alkaline earth metal salts are generally prepared by the reaction of the hydroxide form of the desired metal salt with a compound of formula I.

Acids commonly employed to form such salts include inorganic acids, for example hydrochloric, hydrobromic, nitric, sulphuric or phoshoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, methane-sulfonic or naphthalene-2-sulphonic acid.

In addition to pharmaceutically-acceptable salts, other salts are included in the invention. They may serve as intermediates in the purification of compounds or in the preparation of other, for example pharmaceutically-acceptable, acid addition salts, or are useful for identification, characterization or purification.

As shown in Scheme 1 below, compounds of formula I are enzymatically hydrolyzed in vivo to form compounds of formula II, where $R^{13}$ and $R^{14}$ are both hydrogen (a di-acid).

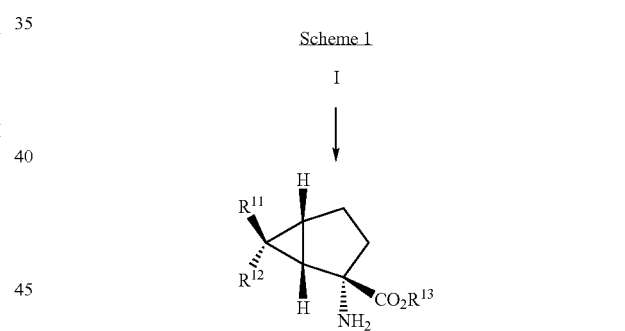

Scheme 1

A variety of physiological functions have been shown to be subject to influence by excessive or inappropriate stimulation of excitatory amino acid transmission. The compounds of formula I the present invention are believed to have the ability to treat a variety of necrological disorders in mammals associated with this condition, including acute neurological disorder such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The compounds of formula I are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable salt thereof.

Compounds of formula I of the present invention are also believed to have the ability to treat a variety of other neurological disorders in mammals that are associated with glutamate dysfunction, including muscular spasms, convulsions, migraine headaches, urinary incontinence, psychosis, (such as schizophrenia), drug tolerance and withdrawal (such as nicotine, opiates and benzodiazepines), anxiety and related disorders, emesis, brain edema, premenstrual dysphoric disorder (PDD), chronic pain, and tardive dyskinesia. The compounds of formula I are also useful as antidepressant and analgesic agents. Therefore, the present invention also provides methods for treating these disorders which comprise administering to a patient in need thereof an effective amount of the compound of formula I, or a pharmaceutically acceptable salt thereof.

A compound of formula I may be made by a process which is analogous to one known in the chemical art for the production of structurally analogous heterocyclic compounds or by a novel process described herein. Such processes and intermediates useful for the manufacture of a compound of formula I as defined above are provided as further features of the invention and are illustrated by the following procedures in which, unless otherwise specified, the meanings of the generic radicals are as defined above.

(A) For a compound of formula I in which $R^{13}$ is not hydrogen and $R^{14}$ is hydrogen, deprotecting the amine group of a compound of formula III

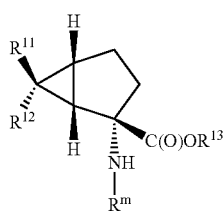

III in which $R^m$ is an amine-protecting group as described in General Procedure 4.

(B) For a compound of formula III in which $R^{13}$ is not hydrogen and $R^{14}$ is hydrogen, ring-opening a compound of formula IV as described in General Procedure 1.

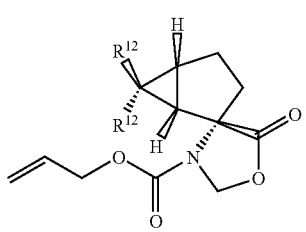

IV

The term "amine protecting group," as used herein, refers to those groups intended to protect or block the amine group against undesirable reactions during synthetic procedures. Choice of the suitable amine protecting group used will depend upon the conditions that will be employed in subsequent reaction steps wherein protection is required, as is well within the knowledge of one of ordinary skill in the art.

Commonly used amine protecting groups are disclosed in T. W. Greene and P. G. M. Wuts, Protective Groups In Organic Synthesis, 3$^{nd}$ Ed. (John Wiley & Sons, New York (1999). Suitable amine protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, alpha-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 2-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, alpha, alpha-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred suitable amine protecting groups are formyl, acetyl, methyloxycarbonyl, benzoyl, pivaloyl, allyloxycarbonyl, t-butylacetyl, phenylsulfonyl, benzyl, t-butyloxycarbonyl (Boc) and benzyloxycarbonyl (Cbz). The amine protecting group is decomposed by using a conventional procedure which does not affect another portion of the molecule.

The term "carboxy-protecting group" as used herein refers to one of the ester derivatives of the carboxylic acid group commonly employed to block or protect the carboxylic acid group while reactions are carried out on other functional groups of the compound. Particular values include, for example, methyl, ethyl, tert-butyl, benzyl, methoxymethyl, trimethylsilyl, allyl, and the like. Further examples of such groups may be found in T. W. Greene and P. G. M. Wuts, Protecting Groups in Organic Synthesis, 3$^{nd}$ Ed. (John Wiley & Sons, N.Y. (1999). The ester is decomposed by using a conventional procedure which does not affect another portion of the molecule.

Whereafter, for any of the above procedures, when a pharmaceutically acceptable salt of a compound of formula I is required, it is obtained by reacting the acid of formula I with a physiologically acceptable base or by reacting a basic compound of formula I with a physiologically acceptable acid or by any other conventional procedure.

The term "aryl" represents groups such as phenyl, substituted phenyl, and naphthyl. The term "substituted phenyl", as used herein, represents a phenyl group substituted with one or more moieties chosen from the group consisting of aryl, aryloxy, halogen, hydroxy, cyano, nitro, (1–6C) alkyl, (1–4C) alkoxy, arylalkyloxy, alkoxycarbonyl, protected carboxy, carboxymethyl, hydroxymethyl, amino, protected amino, aminomethyl, or trifluoromethyl. Examples of a substituted phenyl group include 4-chlorophenyl, 2,6-dichlorophenyl, 2,5-dichlorophenyl, 3,5-dichlorophenyl, 3,4-dichlorophenyl, 2,4-dichlorophenyl, 3-chlorophenyl, 2-bromophenyl, 3-bromophenyl, 4-bromophenyl, 3,4-dibromophenyl, 3-chloro-4-fluorophenyl, 2-fluorophenyl, 4-methylphenyl, 2-methylphenyl, 4-ethylphenyl, 4-ethoxy-phenyl 4-propylphenyl, 4-butoxyphenyl, 4-t-butyl-phenyl, 2,3- difluorophenyl, 3,5-difluorophenyl 2,6-difluorophenyl, 2,6-dimethylphenyl, 2,5-dimethylphenyl 3,5-dimethylphenyl, 2,4,6-trifluorophenyl, 2-trifluoromethylphenyl, 2,4-bis(trifluoromethyl)-phenyl, 3,5-bis(trifluoromethyl)phenyl, 2-methoxyphenyl, 3-methoxyphenyl, 3,5-dimethoxyphenyl, 2,3,6-trimethylphenyl, 2-amino-5-methylphenyl, 3-phenoxyphenyl, 3-benzyloxyphenyl, 4-acetoxyphenyl, 2-biphenyl, 5-indanyl and the like.

The term "(1–6C) arylalkyl" represents a straight, branched, or cyclic alkyl group having from one to six carbon atoms substituted with one or more aryl groups. Included in the term "(1–6C) arylalkyl" are substituted benzyl groups such as 2,4-dichlorobenzyl, 4-butoxybenzyl, 2-fluorobenzyl, 2,5-dichlorobenzyl, 2-bromobenzyl, 3,5-difluorobenzyl, 2-methoxybenzyl, 3-chlorobenzyl, 2,6-dichlorobenzyl, 2,4,6-trimethylbenzyl, 3,5-dichlorobenzyl, 2-methylbenzyl, 3,5-dimethylbenzyl, 3-phenoxybenzyl, 4-acetoxybenzyl, 2-phenylbenzyl, 3-fluorobenzyl, 2,5-dimethylbenzyl, 4-butoxybenzyl, 3,5-dimethylbenzyl, 2,3-difluorobenzyl and 2-chlorobenzyl.

The term "(1–6C) heterocyclylalkyl" represents a straight, branched, or cyclic alkyl group having from one to six carbon atoms substituted with one or more heterocyclyl groups. Included in the term "(1–6C) heterocyclylalkyl" are substituted thiophenyl such as thiopen-2-yl methyl and substituted benzothiophenyl such as benzothiophen-2-yl methyl.

The term "heterocyclyl" includes heteroaromatics an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or a 5–6 membered ring containing from one to four heteroatoms selected from oxygen, sulfur and nitrogen. Examples of heteroaromatic groups are furyl, thiophenyl, oxazolyl, isoxazolyl, thiazoyl, isothiazolyl, imidazolyl, pyrimidyl, benzofuryl, benzothiophenyl, benzimidazolyl, benzoxazolyl, benzothiazolyl and indolyl. Examples of particular values are thienyl and benzothienyl.

While all the compounds of formula I of the present invention are believed to provide prodrug forms, producing higher oral exposure of their parent compounds, certain compounds of the current invention are preferred for such use. Preferably, $R^{11}$ is $CO_2R^{14}$, $R^{12}$ and $R^{14}$ are hydrogen, and $R^{13}$ is (1–6C) arylalkyl or (1–6C) heterocyclylalkyl. Representative compounds from this preferred group of formula I compounds include (1S,2S,5R,6S)-2-Amino-bicyclo[3.1.0]hexane-2,6-dicarboxylic acid 2-(2,4-dichlorobenzyl ester) hydrochloride, (1S,2S,5R,6S)-2-Amino-bicyclo[3.1.0]hexane-2,6-dicarboxylic acid 2-(4-butoxybenzyl ester) hydrochloride, (1S,2S,5R,6S)-2-Amino-bicyclo[3.1.0]hexane-2,6-dicarboxylic acid 2-(2-fluorobenzyl ester) hydrochloride, (1S,2S,5R,6S)-2-Amino-bicyclo[3.1.0]hexane-2,6-dicarboxylic acid 2-(2-trifluoromethyl- benzyl ester) hydrochloride, (1S,2S,5R, 6S)-2-Amino-bicyclo[3.1.0]hexane-2,6-dicarboxylic acid 2-(2,5-dichlorobenzyl ester) hydrochloride, (1S,2S,5R,6S)-2-Amino-bicyclo[3.1.0]hexane-2,6-dicarboxylic acid 2-(2'-bromo)benzyl ester hydrochloride, (1S,2S,5R,6S)-2-Amino-bicyclo[3.1.0]hexane-2,6-dicarboxylic acid 2-(3',5'-difluoro)benzyl ester hydrochloride, (1S,2S,5R,6S)-2-Amino-2-(3-chloro-benzyloxycarbonyl)-bicyclo[3.1.0]hexane-6-carboxylic acid, (1S,2S,5R,6S)-2-Amino-2-(2',6'-dichlorobenzyloxycarbonyl)-bicyclo[3.1.0]hexane-6-carboxylic acid hydrochloride, (1S,2S,5R,6S)2-Amino-bicyclo[3.1.0]hexane-2,6-dicarboxylic acid 6-(2',4',6'-trimethyl-benzyl) ester hydrochloride, (1S,2S,5R,6S)2-Amino-bicyclo[3.1.0]hexane-2,6-dicarboxylic acid 2-thiophen-2-yl methyl ester hydrochloride, (1S,2S,5R,6S)-2-Amino-bicyclo[3.1.0]hexane-2,6-dicarboxylic acid 2-(2'-phenyl)benzyl ester hydrochloride, (1S,2S,5R,6S)-2-Amino-bicyclo[3.1.0]hexane-2,6-dicarboxylic acid 2-(2',5'-dimethyl)benzyl ester hydrochloride, (1S,2S,5R,6S)-2-Amino-bicyclo[3.1.0]hexane-2,6-dicarboxylic acid 2-(2-methyl-benzyl) ester hydrochloride, (1S,2S,5R,6R)-2-Amino-bicyclo[3.1.0]hexane-2,6-dicarboxylic acid 6-(3,5-dimethyl-benzyl)ester hydrochloride, 2-Amino-bicyclo[3.1.0]hexane-2,6-dicarboxylic acid 2-(3-phenoxy-benzyl) ester hydrochloride, (1S,2S,5R,6S)-2-Amino-2-(4-acetoxy-benzyloxycarbonyl)-bicyclo[3.1.0]hexane-6-carboxylic acid hydrochloride, (1S,2S,5R,6S)-2-Amino-bicyclo[3.1.0]hexane-2,6-dicarboxylic acid 2-(2'-methoxy)benzyl ester, (1S,2S,5R,6S)-2-Amino-2-benzhydryloxycarbonyl-bicyclo[3.1.0]hexane-6-carboxylic acid, (1S,2S,5R,6S)2-Amino-bicyclo[3.1.0]hexane-2,6-dicarboxylic acid 2-thiophen-2-yl-methyl ester, (1S,2S,5R,6S)2-Amino-bicyclo[3.1.0]hexane-2,6-dicarboxylic acid 6-(3,5-dichloro-benzyl) ester, (1S,2S, 5R,6S)-2-Amino-2-(2,3-difluorobenzyloxycarbonyl)-bicyclo[3.1.0]hexane-6-dicarboxylic acid, (1S,2S,5R,6S)-2-Amino-2-(2-butoxy-benzyloxycarbonyl)-bicyclo[3.1.0]hexane-6-carboxylic acid, (1S,2S,5R,6S)-2-Amino-bicyclo[3.1.0]hexane-2,6-dicarboxylic acid 2-(3'-fluoro)benzyl ester, (1S,2S,5R,6S)-2-Amino-bicyclo[3.1.0]hexane-2,6-dicarboxylic acid 2-(2,5-difluorobenzyl ester), and (1S,2S,5R, 6S)2-Amino-bicyclo[3.1.0]hexane-2,6-dicarboxylic acid 2-benzo[b]thiophen-2'-yl methyl ester.

While all the compounds of formula III of the present invention where $R^m$ is an amine protecting group are believed to be useful for the synthesis of compounds of formula I, certain compounds are preferred. Preferably, $R^m$ is allyloxycarbonyl, $R^{13}$ is hydrogen, and $R^{14}$ is a carboxy protecting group, for example an allyl group; or $R^m$ is tert-butoxycarbonyl, and $R^{13}$ and $R^{14}$ are both hydrogen.

Also useful for the synthesis of compounds of formula I are compounds where the C-2 amino and carboxy groups of the cyclopentane ring are protected in the form of a cyclized ring. Preferably, the cyclized ring is an oxazolidinone that is spiro fused to the 2-postion of bicyclo[3.1.0]hexane-6-carboxylic acid, for example a compound of formula IV.

The compounds of formula I of the present invention are generally synthesized from compounds of formula II where $R^{11}$ is $C(O)OR^{14}$ and $R^{12}$, $R^{13}$ and $R^{14}$ are all hydrogen. The compounds of formula II are prepared as described in U.S. Pat. No. 5,750,566 which is incorporated by reference in its entirety.

Generally, compounds of formula I in which $R^{13}$ is (1–6C) heterocyclylalkyl, aryl, or (1–6C) arylalkyl may be prepared by reacting compounds of formula III in which $R^{13}$ is hydrogen and $R^m$ is an amine protecting group with esterifying agents. Examples of esterifying agents include a) an alcohol in the presence of a coupling reagent such as a carbodiimide or b) a halide in the presence of a base. Alternatively, compounds of formula I in which $R^{13}$ is (1–6C) heterocyclylalkyl, aryl, or (1–6C) arylalkyl may be prepared by reacting compounds of formula IV where $R^{14}$ is hydrogen with an alcohol in the presence of a base.

More specifically, compounds of formula II are reacted with amine protecting agents such as allyl chloroformate in the presence of a suitable aqueous base such as sodium bicarbonate in a suitable solvent such as dioxane to produce compounds of formula III in which $R^m$ is allyloxycarbonyl.

Compounds of formula III are reacted with carboxy protecting agents such as allyl alcohol, EDCI and HOBt in the presence of a suitable base such as triethylamine in a convenient solvent such as dichloromethane to provide compounds of formula V as shown in scheme 2.

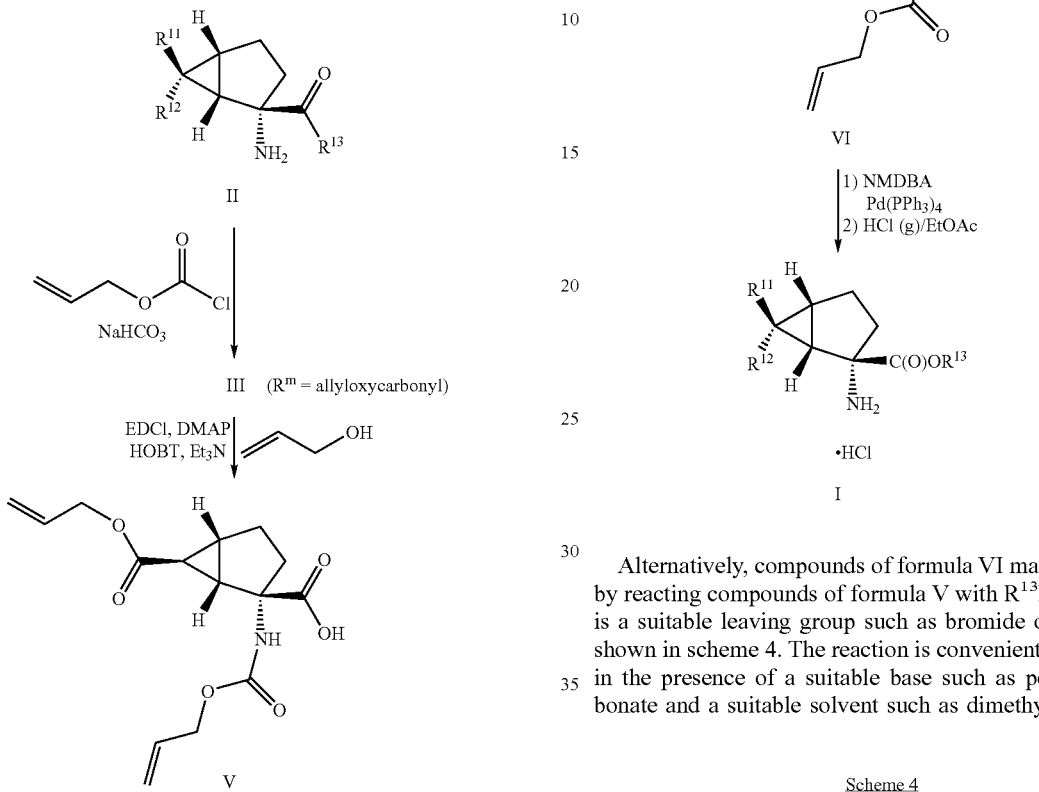

Compounds of formula V are reacted with a carbodiimide such as EDCI and an alcohol of formula $HOR^{13}$ to provide compounds of formula VI in which $R^{13}$ is not hydrogen as shown in scheme 3. The reaction is conveniently performed in the presence of activating agents such as hydroxybenzotriazole and dimethylaminopyridine. Convenient solvents include dichloromethane.

Compounds of formula VI are reacted with a metal catalyst such as tetrakistriphenyl phosphine palladium(O) to produce compounds of formula I in which $R^{14}$ is hydrogen. The reaction is performed in the presence of a metal catalyst regenerating agent such as 1,3-dimethylbarbituric acid in a convenient solvent such as dichloromethane. The acid addition salts may be prepared by the reaction of an acid such as hydrogen chloride gas with a compound of formula I. Convenient solvents include ethyl acetate.

Scheme 3

V

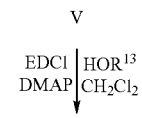

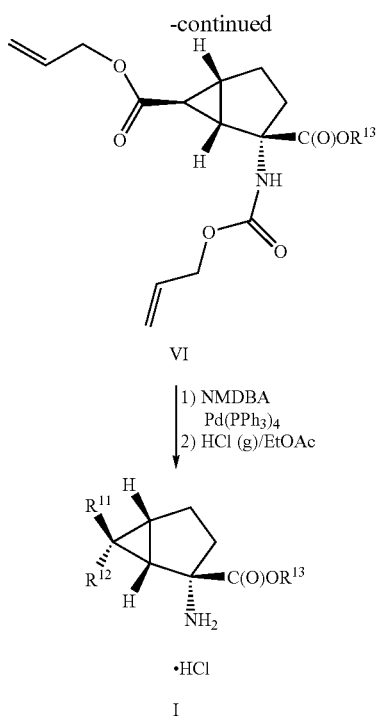

Alternatively, compounds of formula VI may be prepared by reacting compounds of formula V with $R^{13}X$ in which X is a suitable leaving group such as bromide or chloride as shown in scheme 4. The reaction is conveniently carried out in the presence of a suitable base such as potassium carbonate and a suitable solvent such as dimethylformamide.

Scheme 4

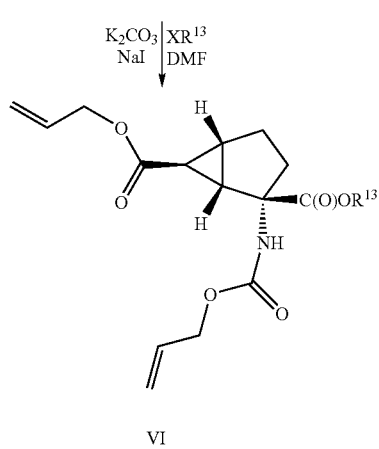

Alternatively, compounds of formula II are reacted with amine protecting agents such as di-tert-butyl dicarbonate in the presence of a suitable aqueous base such as sodium hydroxide in a suitable solvent such as dioxane to produce compounds of formula III in which $R^m$ is tert-butyloxycarbonyl. Compounds of formula III are reacted with $R^{13}X$ in which X is a suitable leaving group such as bromide or chloride to produce compounds of formula VII as shown in scheme 5. The reaction is conveniently carried out in the presence of a suitable base such as potassium carbonate and a suitable solvent such as dimethylformamide.

Compounds of formula VII are reacted with amine deprotecting agents such as hydrogen chloride in a suitable solvent such as ethyl acetate to produce compounds of I as the hydrochloride salt.

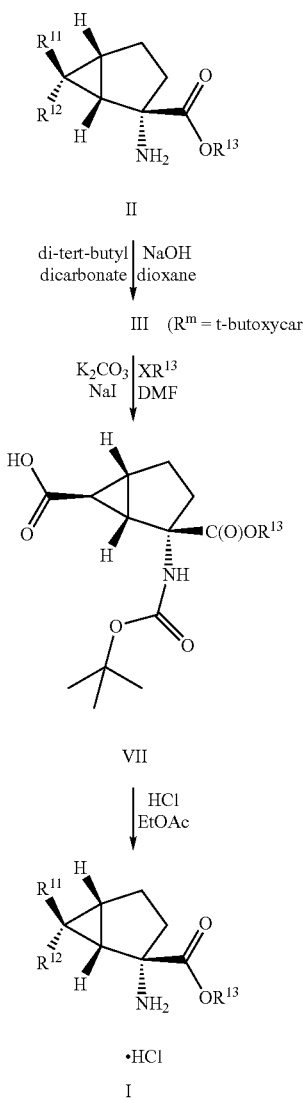

n-butyl lithium to provide compounds of formula X. Convenient solvents include tetrahydrofuran.

Compounds of formula X are reacted with a metal catalyst such as tetrakistriphenyl phosphine palladium(O) to produce compounds of formula I in which $R^{15}$ is hydrogen. The reaction is performed in the presence of a metal catalyst regenerating agent such as 1,3-dimethylbarbituric acid in a convenient solvent such as dichloromethane. The acid addition salts may be prepared by the reaction of an acid such as hydrogen chloride gas with a compound of formula I. Convenient solvents include ethyl acetate.

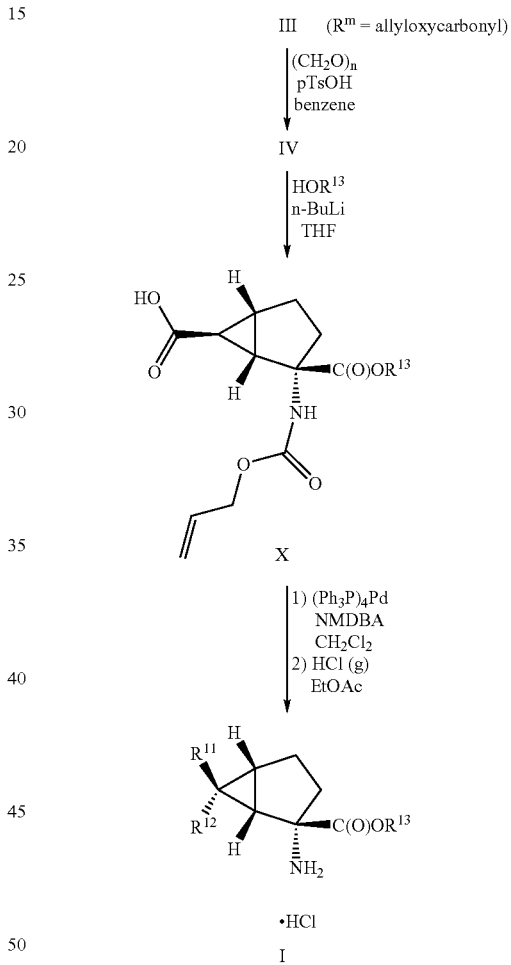

Alternatively, compounds of formula I in which $R^{14}$ is hydrogen may be prepared by reacting compounds of formula IV as shown in scheme 6. More specifically, compounds of formula IV may be prepared by reacting compounds of formula III in which $R^m$ is an amine protecting group such as allyloxycarbonyl with an aldehyde such as paraformaldehyde in the presence of a suitable acid catalyst such as para-toluenesulphonic acid. The reaction may be carried out in a suitable solvent such as benzene with convenient removal of water such as azetropic distillation.

Compounds of formula IV are reacted with an alcohol of formula $HOR^{13}$ in the presence of a suitable base such as The term "affecting" refers to a formula I compound acting as an agonist at an excitatory amino acid receptor. The term "excitatory amino acid receptor" refers to a metabotropic glutamate receptor, a receptor that is coupled to cellular effectors via GTP-binding proteins. The term "cAMP-linked metabotropic glutamate receptor" refers to a metabotropic receptor that is coupled to inhibition of adenylate cyclase activity.

The term "neurological disorder" refers to both acute and chronic neurodegenerative conditions, including cerebral deficits subsequent to cardiac bypass surgery and grafting, cerebral ischemia (for example stroke resulting from cardiac arrest), spinal cord trauma, head trauma, Alzheimer's Disease, Huntington's Chorea, amyotrophic lateral sclerosis, AIDS-induced dementia, perinatal hypoxia, hypoglycemic neuronal damage, ocular damage and retinopathy, cognitive disorders, idiopathic and drug-induced Parkinson's Disease. This term also includes other neurological conditions that are caused by glutamate dysfunction, including muscular spasms, migraine headaches, urinary incontinence, drug tolerance, withdrawal, and cessation (i.e. opiates, benzodiazepines, nicotine, cocaine, or ethanol), smoking cessation, emesis, brain edema, chronic pain, sleep disorders, convulsions, Tourette's syndrome, attention deficit disorder, and tardive dyskinesia.

The term "psychiatric disorder" refers to both acute and chronic psychiatric conditions, including schizophrenia, anxiety and related disorders (e.g. panic attack and stress-related cardiovascular disorders), depression, bipolar disorders, psychosis, and obsessive compulsive disorders.

A particular aspect of the present invention includes a method for affecting the cAMP-linked metabotropic glutamate receptors in a patient, which comprises administering to a patient requiring modulated excitatory amino acid neurotransmission a pharmaceutically-effective amount of a compound of formula I.

Another particular aspect of the present invention includes a method of administering an effective amount of a compound of formula II, where $R^{13}$ and $R^{14}$ are both hydrogen (a di-acid), which comprises administering to a patient requiring modulated excitatory amino acid neurotransmission a pharmaceutically effective amount of a compound of formula I.

Another particular aspect of the present invention includes a method for treating a psychiatric disorder in a patient which comprises administering to the patient in need of treatment thereof a pharmaceutically-effective amount of a compound of formula I.

Another particular aspect of the present invention includes a method for treating a neurological disorder in a patient which comprises administering to the patient in need of treatment thereof a pharmaceutically-effective amount of a compound of formula I.

A preferred method for treating a psychiatric disorder in a patient comprises administering to the patient in need thereof a pharmaceutically-effective amount of a compound of formula I wherein said psychiatric disorder is schizophrenia, anxiety and related disorders, depression, dipolar disorders, psychosis, and obsessive compulsive disorders.

A preferred method for treating a neurological disorder in a patient comprises administering to the patient in need thereof a pharmaceutically-effective amount of a compound of formula I wherein said neurological disorder is cerebral deficits subsequent to cardiac bypass and grafting; cerebral ischemia; spinal cord trauma; head trauma; Alzheimer's Disease; Huntington's Chorea; amyotrophic lateral sclerosis; AIDS-induced dementia; perinatal hypoxia; hypoglycemic neuronal damage; ocular damage and retinopathy; cognitive disorders; idiopathic and drug-induced Parkinsons' Disease; muscular spasms; migraine headaches; urinary incontinence; drug tolerance, withdrawal, and cessation; smoking cessation; emesis; brain edema; chronic pain; sleep disorders; convulsions; Tourette's syndrome; attention deficit disorder; and tardive dyskinesia.

A more preferred method for treating a psychiatric disorder in a patient comprises administering to the patient in need thereof a pharmaceutically-effective amount of a compound of formula I wherein said psychiatric disorder is anxiety and related disorders.

A more preferred method for treating a neurological disorder in a patient comprises administering to the patient in need thereof a pharmaceutically-effective amount of a compound of formula I wherein said neurological disorder is drug tolerance, withdrawal, and cessation; or smoking cessation.

An additional aspect of the present invention is a compound of formula I, or a pharmaceutically acceptable salt thereof, for use as a pharmaceutical.

Another aspect of the present invention includes the use of a compound of formula I, or a pharmaceutically acceptable salt thereof, for the manufacture of a medicament for treating neurological or psychiatric disorders.

If not commercially available, the necessary starting materials for the above procedures may be made by procedures which are selected from standard techniques of organic and heterocyclic chemistry, techniques which analogous to the syntheses of known, structurally similar compounds, and the procedures described in the Examples, including novel procedures.

As used herein the term "effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances. For example, a typical daily dose may contain from about 25 mg to about 300 mg of the active ingredient. The compounds can be administered by a variety of routes including oral, rectal, transdermal, subcutaneous, intravenous, intramuscular, bucal or intranasal routes. Alternatively, the compound may be administered by continuous infusion.

As used herein the term "patient" refers to a mammal, such as a mouse, guinea pig, rat, dog or human. It is understood that the preferred patient is a human.

The term "treating" (or "treat") as used herein includes its generally accepted meaning which encompasses prohibiting, preventing, restraining, and slowing, stopping or reversing progression of a resultant symptom. As such, the methods of this invention encompass both therapeutic and prophylactic administration.

The ability of compounds to modulate metabotropic glutamate receptor function may be demonstrated by examining their ability to influence either cAMP production (mGluR 2, 3, 4, 6, 7 or 8) or phosphoinositide hydrolysis (mGluR 1 or 5) in cells expressing these individual human metabotropic glutamate receptor (mGluR) subtypes. (D. D. Schoepp, et al., *Neuropharmacol.*, 1996, 35, 1661–1672 and 1997, 36, 1–11).

The ability of formula I compounds to treat anxiety or a related disorder may be demonstrated using the well known fear potentiated startle and elevated plus maze models' of anxiety described respectively in Davis, Psychopharmacology, 62:1;1979 and Lister, Psychopharmacol, 92:180–185; 1987

In Vivo Exposure as Measured by Rat Plasma Concentration

To study the in vivo exposure of LY354740 following oral dosing of compounds of the present invention in comparison to LY354740, studies measuring the plasma concentrations of LY354740 in rats were performed.

Mature Fischer 344 male rats (190–270 gram) were obtained from Harlan Sprague-Dawley, Cumberland, Ind., USA and acclimated in the study housing for 3 days. On day 4, test compounds were dissolved in buffered water (1 mg/ml=test compound/20 mM potassium dihydrogen phosphate, pH=2) and given orally as a single 5 mg/kg dose. Blood samples were collected through orbital sinus or cardiac puncture (last time point) at 0.5 and 1 hour or, alternatively, 1 and 3 hours. Plasma samples were stored at −20° C. in the presence of phenylmethylsulfonyl fluoride, a protease inhibitor, prior to analysis. Plasma samples and internal standard compounds were pretreated by solid phase extraction (SAX support, methanol/water/dilute acetic acid). The plasma concentrations (ng/ml) of LY354740 for each test compound were determined by LC/MS/MS and are presented as a sum of the concentrations at the 0.5 and 1 hour or, alternatively, 1 and 3 hour sample time points as shown in table 1.

TABLE 1

Comparison of plasma concentrations of LY354740 and compounds of the present invention

| Compound (@5 mg/kg p. o.) | Plasma Concentration of LY354740, ng/ml (sum of 0.5 and 1 hour) |
|---|---|
| LY354740 | 466 |
| Example 29 | 3000 |
| Example 30 | 2560 |
| Example 31 | 2529 |
| Example 33 | 1696 |
| Example 34 | 4104 |
| Example 35 | 1712 |
| Example 36 | 1459 |
| Example 37 | 1895 |
| Example 38 | 2617 |
| Example 39 | 3622 |
| Example 40 | 4945 |
| Example 41 | 1620 |
| Example 42 | 1816 |
| Example 43 | 1509 |
| Example 44 | 1967 |
| Example 45 | 4259 |
| Example 46 | 2420 |
| Example 47 | 2956 |
| Example 48 | 4887 |
| Example 49 | 2192 |
| Example 50 | 2530 |
| Example 51 | 2216 |
| Example 52 | 1724 |
| Example 53 | 4240 |
| Example 54 | 2530 |
| Example 56 | 2389 |

The compounds of the present invention are preferably formulated prior to administration. Therefore, another aspect of the present invention is a pharmaceutical formulation comprising a compound of formula I a pharmaceutically acceptable metabolically labile ester thereof, or a pharmaceutically acceptable salt thereof, and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

The following Examples further illustrate the compounds of the present invention and the methods for their synthesis. The Examples are not intended to be limiting to the scope of the invention in any respect, and should not be so construed. All experiments were run under a positive pressure of dry nitrogen or argon. All solvents and reagents were purchased from commercial sources and used as received, unless otherwise indicated. Dry tetrahydrofuran (THF) was obtained by distillation from sodium or sodium benzophenone ketyl prior to use. Proton nuclear magnetic resonance ($^1$H NMR) spectra were obtained on a GE QE-300 spectrometer at 300.15 MHz, a Bruker AM-500 spectrometer at 500 MHz, a Bruker AC-200P spectrometer at 200 MHz or a Varian Inova at 500 MHz. Free atom bombardment mass spectroscopy (PABMS) was performed on a VG ZAB-2SE instrument. Field desorption mass spectroscopy (FDMS) was performed using either a VG 70SE or a Varian MAT 731 instrument. Optical rotations were measured with a Perkin-Elmer 241 polarimeter. Chromatographic separation on a Waters Prep 500 LC was generally carried out using a linear gradient of the solvents indicated in the text. The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 mL of 10% aqueous sulfuric acid] and then heated on a hot plate). Flash or silica gel chromatography was performed as described by Still, et al. Still, Kahn, and Mitra, *J. Org. Chem.*, 43, 2923 (1978). Elemental analyses for carbon, hydrogen, and nitrogen were determined on a Control Equipment Corporation 440 Elemental Analyzer, or were performed by the Universidad Complutense Analytical Centre (Facultad de Farmacia, Madrid, Spain). Melting points were determined in open glass capillaries on a Gallenkamp hot air bath melting point apparatus or a Buchi melting point apparatus, and are uncorrected. The number in parenthesis after the compound name refers to the compound number.

The abbreviations, symbols and terms used in the examples have the following meanings.

Ac=acetyl
AcOH=acetic acid
AllocCl=allyl chloroformate
Anal.=elemental analysis
Bn or Bzl=benzyl
Bu=butyl
BOC=butoxycarbonyl
calcd=calculated
D$_2$O=deuterium oxide
DCC=dicyclohexylcarbodiimide
DIBAL-H=diisobutyl aluminum hydride
DMAP=dimethylaminopyridine
DMF=dimethylformamide
DMSO=dimethylsulfoxide
EDCI=N-ethyl-N'N'-dimethylaminopropyl carbodiimide
Et=ethyl
EtOAc=ethyl acetate
EtOH=ethanol
FAB=Fast Atom Bombardment (Mass Spectroscopy)
FDMS=field desorption mass spectrum
HOAt=1-hydroxy-7-azabenzotriazole
HOBt=1-hydroxybenzotriazole
HPLC=High Performance Liquid Chromatography
HRMS=high resolution mass spectrum
i-PrOH=isopropanol
IR=Infrared Spectrum
L=liter
Me=methyl
MeOH=methanol
MPLC=Medium Pressure Liquid Chromatography
Mp=melting point
MS=Mass Spectroscopy
MTBE=t-butyl methyl ether
NBS=N-bromosuccinimide
NMDBA=1,3-dimethylbarbituric acid
NMR=Nuclear Magnetic Resonance
p-TsOH=para-toulenesulphonic acid
Ph=phenyl
p.o.=oral administration
i-Pr=isopropyl
Rochelle's Salt=potassium sodium tartrate
SM=starting material
TBS=tert-butyldimethylsilyl
TEA=triethylamine
Temp.=temperature
TFA=trifluoroacetic acid
THF=tetrahydrofuran
TLC=thin layer chromatography
t-BOC=tert-butoxycarbonyl

EXAMPLE PREPARATION 1

Synthesis of (1S,2S,5R,6S)-2-Allyloxycarbonylamino-bicyclo[3.1.0]hexane-2,6-dicarboxylic acid

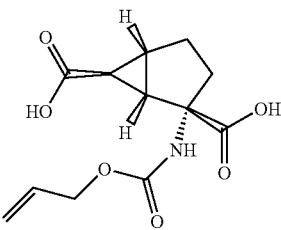

(1S,2S,5R,6S)-2-Amino-bicyclo[3.1.0]hexane-2,6-dicarboxylic acid (15.0 g, 73.9 mmol) was slowly dissolved in 250 mL of saturated sodium bicarbonate. After complete solution, dioxane (100 mL) and allyl chloroformate (15.7 mL, 147.8 mmol) were added at room temperature and the mixture was stirred overnight. The reaction mixture was diluted with water (100 mL) and washed with three portions of ethyl acetate. The organic layer was extracted once with saturated sodium bicarbonate. The combined aqueous layers were acidified to pH 1 with 4N hydrochloric acid and extracted with two portions of ethyl acetate. The organic layer was dried over magnesium sulfate, filtered and concentrated to provide the title compound as an oil (13.4 g, 67% yield).

$^1$H-NMR (CD$_3$OD)δ: 6.01–5.82 (m, 1H); 5.35–5.13 (m, 2H); 4.51 (d, J=5.1 Hz, 2H); 2.48–1.78 (m, 5H); 1.69–1.62 (m, 1H); 1.45–1.29 (m, 1H). $^{13}$C-NMR (CD$_3$OD)δ: 176.7, 176.6, 158.3, 134.2, 117.4, 67.3, 66.3, 35.8, 33.1, 29.9, 27.0, 22.0.

EXAMPLE PREPARATION 2

Synthesis of (1'S,2'S,5'R,6'S)-3-Allyloxycarbonyl-5-oxo-oxazolidinone-4-spiro-2'-bicyclo[3.1.0]hexane-6'-carboxylic acid

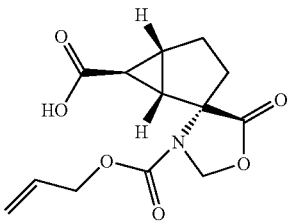

(1S,2S,5R,6S)-2-Allyloxycarbonylamino-bicyclo[3.1.0]hexane-2,6-dicarboxylic acid (19.17 g, 64.33 mmol), paraformaldehyde (7.73 g, 257.32 mmol) and p-toluenesulphonic acid (0.612 f, 3.216 mmol) were slurried in 200 mL of benzene and refluxed with azeotropic removal of water for two hours. The mixture was cooled to room temperature and diluted with 200 mL of Ethyl acetate, washed twice with brine and dried over magnesium sulfate. Concentration afforded the title compound as a slightly hygroscropic solid (17.6 g, 97%). >95% pure by NMR.

$^1$H-NMR (CDCl$_3$, 200.15 MHz): 6.10–5.90 (m, 1H); 5.41–5.21 (m, 4H); 4.65 (dt, J=5.6, 1.3 Hz, 2H); 2.51–2.49

(m, 1H); 2.33–2.18 (m, 2H); 2.04–1.92 (m, 3H); 1.75–1.70 (m, 1H). $^{13}$C-NMR (CD$_3$OD, 50 MHz): 176.1, 175.4, 153.0, 133.5, 118.9, 78.4, 67.8, 67.4, 33.1, 27.2 (×2), 26.0, 23.9.

EXAMPLE PREPARATION 3

Synthesis of (1S,2S,5R,6S)-2-Allyloxycarbonylamino-bicyclo[3.1.0]hexane-2,6-dicarboxylic acid 6-allyl ester

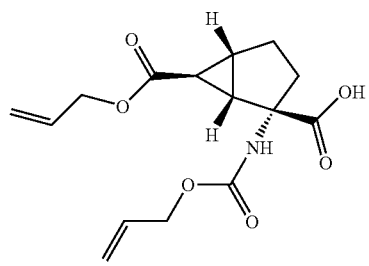

(1S,2S,5R,6S)-2-Allyloxycarbonylamino-bicyclo[3.1.0]hexane-2,6-dicarboxylic acid (13.4 g, 49.81 mmol, 1.0 equiv) was suspended in methylene chloride (400 mL). N-Ethyl-N'-dimethylaminopropylcarbodiimide (9.55 g, 49.81 mmol, 1.0 equiv) and dimethylaminopyridine (0.608 g, 4.98 mmol, 0.1 equiv) were added at room temperature under nitrogen. After a solution formed, allyl alcohol (3.4 mL, 2.89 g, 49.81 mmol, 1.0 equiv) was added and the mixture was stirred overnight at room temperature. The reaction mixture was diluted with methylene chloride and washed twice with water. The organic phase was dried over magnesium sulfate, filtered and concentrated. The title compound was obtained as an oil (44% yield).

$^1$H-NMR (CD$_3$OD, 200.15 MHz): 6.01–5.82 (m, 1H); 5.35–5.13 (m, 2H); 4.51 (d, J=5.1 Hz, 2H); 2.48–1.78 (m, 5H); 1.69–1.62 (m, 1H); 1.45–1.29 (m, 1H).

EXAMPLE PREPARATION 4

Synthesis of (1S,2S,5R,6S)-2-tert-Butoxycarbonylamino-bicyclo[3.1.0]hexane-2,6-dicarboxylic acid

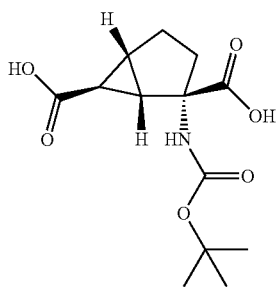

A 1 L flask was charged with (1S,2S,5R,6S)-2-amino-bicyclo[3.1.0]hexane-2,6-dicarboxylic acid monohydrate (24.4 g, 0.12 mol, 1 equiv), dioxane (200 mL) and di-tert-butyl dicarbonate (52.4 g, 0.24 mol, 2.0 equiv). The suspension was vigorously stirred while sodium hydroxide 1N (420 mL, 3.5 equiv) was added. The mixture was stirred for 2 days, then 2.0 more equiv of di-tert-butyl dicarbonate were added and the reaction stirred for 3 additional days at rt. After 5 total days of reaction, water (400 mL) was added to dissolve the salts. The aqueous layer was extracted with ethyl acetate (4×100 mL) to remove the excess of reagent, and then taken to ca. pH=2 using 6 N hydrochloric acid. The acidic aqueous phase was then extracted using ethyl ether (6×200 mL). The combined organic layers were washed with water (250 mL) and brine (250 mL). After drying over sodium sulfate, solvents were evaporated in vacuum to afford a foamy white solid (26.4 g).

77% Yield. mp 100–101° C.

$[\alpha]_D^{25}$=–41.1° (c=1.0, MeOH).

$^1$H NMR (Methanol-d$_4$) δ: 4.98 (brs, 1H), 2.44 (dd, 1H, J=6.2, 2.6 Hz), 2.19–1.92 (m, 4H), 1.62 (t, 1H, J=2.8 Hz), 1.43 (s, 9H), 1.29 (m, 1H).

$^{13}$C NMR (Methanol-d$_4$) δ: 175.6, 175.2, 158.2, 60.1, 34.6, 31.9, 28.4, 27.2, 25.6, 20.6.

MS (Neg. Electrospray): 284.2 (M$^+$–H).

EXAMPLE PREPARATION 5

Synthesis of (2-Butoxy-phenyl)-methanol

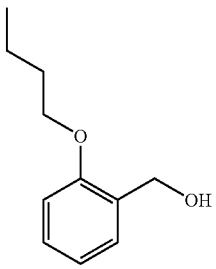

2-Hydroxymethyl phenol (1.2 g, 9.6 mmol) was dissolved in 10 mL of dry acetonitrile. Potassium carbonate (1.3 g, 9.6 mmol) and 1-iodobutane (1 mL, 8.8 mmol) were added and the reaction was stirred at room temperature for 3 days and at 50° C. for 1 day. The solvent was removed and the residue partitioned between ethyl acetate and 1N hydrochloric acid. The acidic aqueous layer was extracted with ethyl acetate (3×25 mL). The combined organic extracts were washed with 0.5 N sodium hydroxide (3×20 mL), dried over MgSO$_4$, filtered and concentrated to provide the title compound (800 mg, 50% yield) as a colorless oil.

$^1$H NMR (CDCl$_3$) δ: 7.32–7.20 (m, 2H), 7.0–6.85 (m, 2H), 4.70 (bs, 2H), 4.05 (t, J=7 Hz, 2H), 2.40 (bs, 1H), 1.89–1.72 (m, 2H), 1.59–1.42 (m, 2H), 0.98 (t, J=7 Hz, 3H).

EXAMPLE PREPARATION 6

Synthesis of Benzo[b]thiophene-2-carbaldehyde

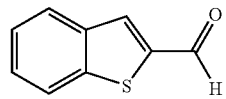

To a solution of benzothiophene (2 g, 14.9 mmol) in 100 mL of THF cooled to −78° C. was added 1.6 M n-butyl lithium in hexanes (10.25 mL, 16.39 mmol). The mixture was stirred at −78° C. for 1 h, warmed to 0° C., stirred for 5 min, recooled to −78° C. and treated with DMF (4.62 mL, 59.61 mmol). The temperature was allowed to rise slowly overnight. The reaction was quenched with saturated aqueous ammonium chloride and extracted with diethyl ether. The combined organic extracts were washed with water and brine, dried over $MgSO_4$ and concentrated to afford the title compound as an oil. (2.216 g, 91%).

$^1$H-NMR (CDCl$_3$, 200.15 MHz): 10.08 (s, 1H); 7.94–7.84 (m, 2H); 7.45 (dquintets, J=7.7, 1.5 Hz, 1H).

EXAMPLE PREPARATION 7

Synthesis of Benzo[b]thiophene-2-methanol

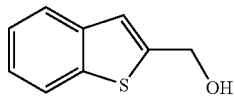

A solution of benzo[b]thiophene-2-carbaldehyde (2.216 g, 13.66 mmol) in THF (60 mL) was reacted with sodium borohydride (0.517 g, 13.66 mmol) at room temperature for 3 h. The reaction was quenched with 1N hydrochloric acid at 0° C., the THF evaporated under vacuum and the aqueous residue extracted with diethyl ether. The organic extract was washed with brine, dried over $MgSO_4$ and concentrated to afford the title compound as a yellow solid (2.23 g, 98%).

$^1$H-NMR (CDCl$_{3-200.15}$ MHz): 7.82–7.68 (m, 2H); 7.36–7.23 (m, 2H); 7.19 (t, J=1.1 Hz, 1H); 4.90 (d, J=1.1 Hz, 2H);

GENERAL PROCEDURE 1

General Procedure for Allyl-Oxazolidinone Opening

The corresponding alcohol (4.0 equiv) was dissolved in dry tetrahydrofuran (1.0 M solution) and n-butyllithium (1.6 M in hexane, 3.5 equiv) was added at −78° C. under nitrogen. After 15 min, the solution was transferred dropwise via cannula to a solution of allyl-oxazolidinone (example preparation 2, 1.0 equiv) in dry tetrahydrofuran (0.1 M solution) at 0° C. The mixture was stirred at 0° C. for 2 h. A saturated solution of ammonium chloride and water were added. The aqueous phase was acidified with 3N hydrochloric acid to pH 1 and extracted with two portions of ethyl acetate. The combined organic extracts were dried over magnesium sulfate, filtered and concentrated. The crude product was purified by silica gel chromatography.

EXAMPLE 1

(1S,2S,5R,6S)-2-Allyloxycarbonylamino-bicyclo[3.1.0]hexane-2,6-dicarboxylic acid 2-(2',4'-dichlorobenzyl ester)

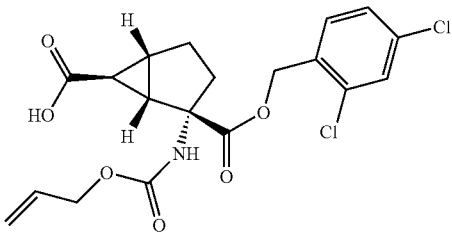

The title compound was prepared according to General Procedure 1 using 2,4-dichlorobenzyl alcohol. 42% yield. Oil.

IR (KBr) ν: 3335, 3084, 2949, 2876, 1740–1690 (br), 1651, 1591, 1564, 1520, 1477, 1450, 1395, 1369, 1332, 1294, 1251, 1180, 1161, 1047 cm$^{-1}$.

$^1$H NMR (CDCl$_3$) δ: 9.84 (br, 1H, CO$_2$H), 7.39 (d, 1H, J=2.0 Hz, C-3'), 7.35 (d, 1H, J=8.2 Hz, C-6'), 7.24 (dd, 1H, J=8.2, 2.0 Hz, C-5'), 5.82 (m, 2H, NH, CH=CH$_2$), 5.23 (s, 2H, CO$_2$CH$_2$), 5.20 (m, 2H, CH=CH$_2$), 4.50 (m, 2H, J=5.2 Hz, CH$_2$CH=CH$_2$), 2.51–2.32 (m, 2H), 2.12–1.90 (m, 3H), 1.70 (t, 1H, J=2.8 Hz), 1.29 (m, 1H).

$^{13}$C NMR (CDCl$_3$) δ: 178.0 (CO$_2$H), 172.3 (CO$_2$CH$_2$), 155.7 (NCOO), 134.82, 134.4, 131.7, 130.9, 129.3, 127.2 (Aromatics), 132.3 (CH=CH$_2$), 117.9 (CH=CH$_2$), 66.6 (C-2), 65.8, 64.2 (CH$_2$CH=CH$_2$, CO$_2$CH$_2$), 35.2 (C-1), 32.3 (C-3), 29.2 (C-5), 26.5 (C-4), 21.1 (C-6).

MS (Electrospray): 428.0 (M$^+$+H).

EXAMPLE 2

(1S,2S,5R,6S)-2-Allyloxycarbonylamino-bicyclo[3.1.0]hexane-2,6-dicarboxylic acid 2-(4'-butoxybenzyl ester)

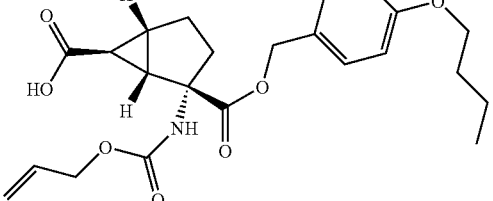

The title compound was prepared according to General Procedure 1 using 4-butoxybenzyl alcohol. 43% yield. Oil.

IR (KBr) ν: 3335, 2957, 2938, 2878, 1740–1699 (br), 1612, 1585, 1514, 1450, 1340, 1296, 1244, 1174, 1068, 1045 cm$^{-1}$. $^1$H NMR (CDCl$_3$) δ: 10.20 (br, 1H, CO$_2$H), 7.25 (d, 2H, J=8.6 Hz, C-2$^-$, C-6$^-$), 6.86 (d, 2H, J=8.6 Hz, C-3', C-5'), 5.80 (m, 2H, NH, CH=CH$_2$), 5.22 (m, 2H, CH=CH$_2$), 5.11 (s, 2H, CO$_2$CH$_2$), 4.50 (m, 2H, CH$_2$CH=CH$_2$), 3.95 (t, 2H, J=6.4 Hz, OCH$_2$), 2.50–2.30 (m, 2H), 2.12–1.68 (m, 6H), 1.49 (st, 2H, CH$_2$CH$_3$), 1.28 (m, 1H), 0.97 (t, 3H, CH$_3$)

$^{13}$C NMR (CDCl$_3$) δ: 178.0 (CO$_2$H), 172.5 (CO$_2$CH$_2$), 159.1, 129.8, 127.3, 114.3 (Aromatics), 155.7 (NCOO), 132.4 (CH=CH$_2$), 117.7 (CH=CH$_2$), 67.6 (CH$_2$), 67.2 (CH$_2$), 66.5 (C-2), 65.7 (CH$_2$), 35.2 (C-1), 32.2 (C-3), 31.1 (CH$_2$), 29.2 (C-5), 26.5 (C-4), 21.0 (C-6), 19.11 (CH$_2$), 13.7 (CH$_3$).

MS (Electrospray): 431.48.

EXAMPLE 3

(1S,2S,5R,6S)-2-Allyloxycarbonylamino-bicyclo[3.1.0]hexane-2,6-dicarboxylic acid 2-(2'-fluorobenzyl ester)

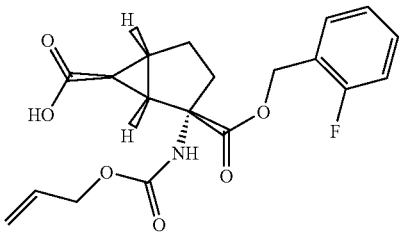

The title compound was prepared according to General Procedure 1 using 2-fluorobenzyl alcohol.

39% yield. Oil.

IR (KBr) ν: 3337, 3051, 2951, 2876, 1701 (br), 1653, 1620, 1589, 1522, 1496, 1456, 1333, 1294, 1250, 1194 cm$^{-1}$. $^1$H NMR (CDCl$_3$) δ: 9.60 (br, 1H, CO$_2$H), 7.35–6.99 (m, 4H, aromatics), 5.82 (m, 1H, CH=CH$_2$), 5.62 (br s, 1H, NH), 5.22 (m, 2H, CH=CH$_2$), 5.22 (s, 2H, CO$_2$CH$_2$), 4.48 (m, 2H, CH$_2$CH=CH$_2$), 2.50–2.30 (m, 2H), 2.18–1.87 (m, 3H), 1.67 (t, 1H, J=2.6 Hz), 1.25 (m, 1H)

$^{13}$C NMR (CDCl$_3$) δ: 178.1 (CO$_2$H), 172.4 (CO$_2$CH$_2$), 160.9 (d, C-2', J=245 Hz), 155.8 (NCOO), 132.3 (CH=CH$_2$), 130.5, 130.3 (2d, C-4', C-6'), 124.1 (d, J=5 Hz, C-5'), 122.6 (d, J=10 Hz, C-1'), 117.9 (CH=CH$_2$), 115.4 (d, J=20 Hz, C-3'), 66.6, 65.8 (C-2, CH$_2$CH=CH$_2$), 61.5 (CO$_2$CH$_2$), 35.2 (C-1), 32.4 (C-3), 29.2 (C-5), 26.6 (C-4), 21.1 (C-6).

MS (Electrospray): 400.1 (M$^+$+Na).

EXAMPLE 4

(1S,2S,5R,6S)-2-Allyloxycarbonylamino-bicyclo[3.1.0]hexane-2,6-dicarboxylic acid 2-(2'-trifluoromethyl)benzyl ester

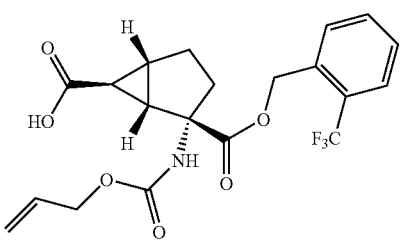

The title compound was prepared according to General Procedure 1 using 2-trifluoromethylbenzyl alcohol.

32% yield. Oil.

IR (KBr) ν: 3335, 3084, 3051, 2961, 2876, 1740–1705 (br), 1651, 1610, 1520, 1456, 1412, 1317, 1253, 1170, 1126, 912 cm$^{-1}$.

$^1$H NMR (CDCl$_3$) δ: 9.70 (br, 1H, CO$_2$H), 7.65 (d, 1H, J=7.4 Hz, aromatic), 7.53 (m, 2H), 7.40 (m, 1H, aromatic), 5.80 (m, 1H, CH=CH$_2$), 5.62 (br s, 1H, NH), 5.35 (s, 2H, CO$_2$CH$_2$), 5.22 (m, 2H, CH=CH$_2$), 4.48 (m, 2H, CH$_2$CH=CH$_2$), 2.50–2.30 (m, 2H), 2.18–1.88 (m, 3H), 1.68 (t, 1H, J=2.8 Hz), 1.31 (m, 1H).

$^{13}$C NMR (CDCl$_3$) δ: 178.0 (CO$_2$H), 172.3 (CO$_2$CH$_2$), 155.9 (NCOO), 133.7 (C-1'), 132.1 (CH=CH$_2$, aromatic), 130.2, 128.4 (aromatics), 128.3 (q, J=30 Hz, C-2'), 126.1 (q, J=5 Hz, C-3'), 124.1 (q, J=270 Hz, CF$_3$), 117.9 (CH=CH$_2$), 66.7 (C-2), 65.9 (CH$_2$CH=CH$_2$), 63.8 (CO$_2$CH$_2$), 35.3 (C-1), 32.5 (C-3), 29.2 (C-5), 26.6 (C-4), 21.1 (C-6).

MS (Electrospray): 450.1 (M$^+$+Na).

EXAMPLE 5

(1S,2S,5R,6S)-2-Allyloxycarbonylamino-bicyclo[3.1.0]hexane-2,6-dicarboxylic acid 2-(2',5'-dichloro)benzyl ester

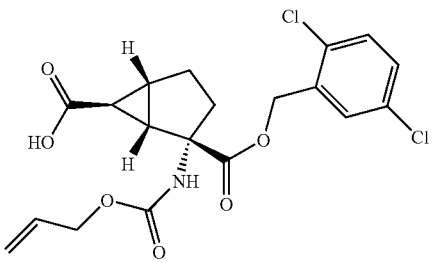

The title compound was prepared according to General Procedure 1 using 2,5-dichlorobenzyl alcohol.

24% yield. Oil.

IR (KBr) ν: 3326, 3090, 2953, 2876, 1709, 1520, 1468, 1451, 1402, 1333, 1294, 1251, 1180, 1161, 1057 cm$^{-1}$.

$^1$H NMR (CDCl$_3$) δ: 10.4 (br, 1H, CO$_2$H), 7.42 (d, 1H, J=2.2 Hz, C-3'), 7.31 (s, 1H, C-6'), 7.27 (m, 1H, C-4'), 5.83 (m, 1H, CH=CH$_2$), 5.63 (br s, 1H, NH), 5.25 (s, 2H, CO$_2$CH$_2$), 5.22 (m, 2H, CH=CH$_2$), 4.55 (d, 2H, J=5.6 Hz, CH$_2$CH=CH$_2$), 2.51–2.32 (m, 2H), 2.12–1.90 (m, 3H), 1.74 (t, 1H, J=2.8 Hz), 1.30 (m, 1H).

$^{13}$C NMR (CDCl$_3$) δ: 178.3 (CO$_2$H), 172.2 (CO$_2$CH$_2$), 155.7 (NCOO), 134.9, 132.9, 131.7, 130.6, 129.7, 129.6 (Aromatics), 132.2 (CH=CH$_2$), 118.1 (CH=CH$_2$), 66.8, 66.1, 64.2 (C-2, CH$_2$CH=CH$_2$, CO$_2$CH$_2$), 35.3 (C-1), 32.6 (C-3), 29.3 (C-5), 26.6 (C-4), 21.2 (C-6).

MS (Electrospray): 450.1 (M$^+$+Na)

EXAMPLE 6

(1S,2S,5R,6S)-2-Allyloxycarbonylamino-bicyclo[3.1.0]hexane-2,6-dicarboxylic acid 2-(2'-bromo)benzyl ester

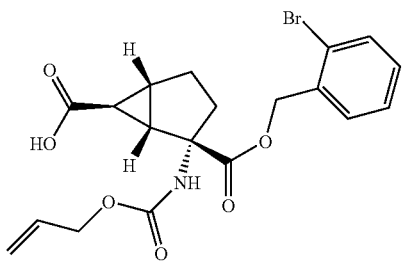

The title compound was prepared according to General Procedure 1 using 2-bromobenzyl alcohol.

43% Yield. Foamy white solid.

$^1$H NMR (CDCl$_3$) δ: 7.57 (dd, 1H, J=7.8, 1.3 Hz), 7.41 (dd, 1H, J=7.7, 1.7 Hz), 7.32 (td, 1H, J=7.4, 1.3 Hz), 7.19 (td, 1H, J=7.7, 2.0 Hz), 5.88 (brs, 1H), 5.79 (m, 1H), 5.29–5.13 (m, 2H), 5.25 (brs, 2H), 4.51 (brd, 2H, J=4.5 Hz), 2.53–2.38 (m, 2H), 2.16–2.90 (m, 3H), 1.72 (t, 1H, J=2.7 Hz), 1.30 (m, 1H)

MS (Electrospray): 437.04.

EXAMPLE 7

(1S,2S,5R,6S)-2-Allyloxycarbonylamino-bicyclo[3.1.0]hexane-2,6-dicarboxylic acid 2-(3',5'-difluoro)benzyl ester

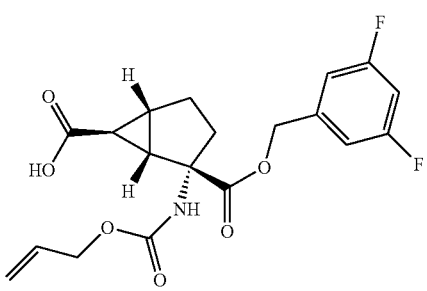

The title compound was prepared according to General Procedure 1 using 3,5-difluorobenzyl alcohol.

48% Yield. Foamy white solid.

$^1$H NMR (CDCl$_3$) δ: 9.52 (brs, 1H), 6.92–6.53 (m, 3H), 5.84 (m, 1H), 5.69 (brs, 1H), 5.31–5.08 (m, 2H), 5.15 (brs, 2H), 4.53 (brd, 2H, J=5.3 Hz), 2.50–2.39 (m, 2H), 2.23–1.94 (m, 3H), 1.73 (t, 1H, J=2.7 Hz), 1.38–1.25 (m, 1H).

EXAMPLE 8

(1S,2S,5R,6S)-2-Allyloxycarbonylamino-bicyclo[3.1.0]hexane-2,6-dicarboxylic acid 2-(2'-methoxy)benzyl ester

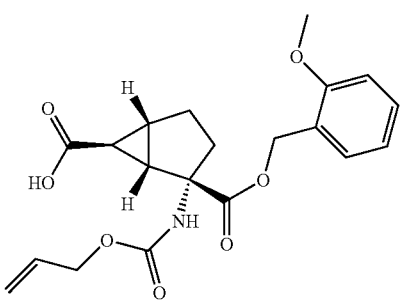

The title compound was prepared according to General Procedure 1 using 2-methoxybenzyl alcohol.

45% Yield. Colorless syrup.

$[\alpha]_D^{25}$=–5.04° (c=1.27, CHCl$_3$).

$^1$H NMR (CDCl$_3$) δ: 7.34–7.27 (m, 2H), 6.97–6.85 (m, 2H), 5.74 (m, 1H), 5.30–5.14 (m, 2H), 5.23 (brs, 2H), 4.51 (m, 2H), 3.82 (s, 3H), 2.53–2.40 (m, 2H), 2.25–1.89 (m, 3H), 1.70 (t, 1H, J=2.7 Hz), 1.33–1.25 (m, 1H).

$^{13}$C NMR (CDCl$_3$) δ: 176.8, 172.5, 157.3, 134.5, 129.4, 123.7, 120.3, 120.2, 117.5, 110.2, 66.6, 65.7, 62.9, 55.1, 35.2, 32.2, 29.1, 26.4, 21.0.

EXAMPLE 9

(1S,2S,5R,6S)-2-Allyloxycarbonylamino-2-benzhydryloxycarbonyl-bicyclo[3.1.0]hexane-6-carboxylic acid

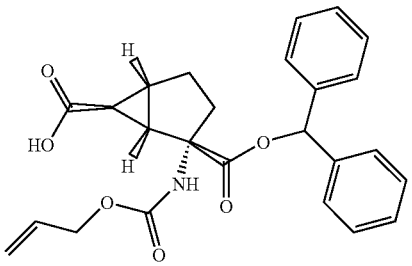

Benzydryl alcohol (2.0 g, 10.9 mmol) was reacted with the allyl-oxazolidinone (1 g, 3.6 mmol) following general procedure 1. Silica gel chromatography (hexanes/EtOAc/AcOH 50:50:1) provided the title compound (837 mg, 53% yield) as a foam.

$^1$H-NMR (CDCl$_3$, 200.15 MHz): 7.32–7.32 (m, 10H); 6.91 (s, 1H); 5.85 (bs, 1H); 5.52 (bs, 1H); 5.18 (bs, 2H); 4.51–4.46 (m, 2H); 2.52 (dd, J=5.9, 2.4 Hz, 1H); 2.41–2.32 (m, 1H); 2.19–1.90 (m, 3H); 1.72 (t, J=2.7 Hz, 1H); 1.39–1.23 (m, 1H).

EXAMPLE 10

(1S,2S,5R,6S)-2-Allyloxycarbonylamino-2-(3'-chloro-benzyloxycarbonyl)-bicyclo[3.1.0]hexane-6-carboxylic acid

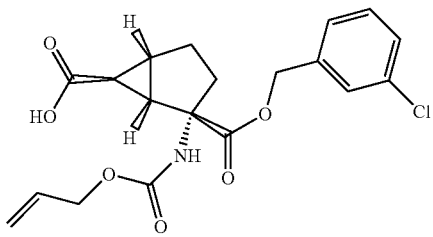

(3-Chlorophenyl)-methanol (1.3 mL, 11.4 mmol) was reacted with the allyl-oxazolidinone (1.1 g, 3.8 mmol) following general procedure 1. Silica gel chromatography (hexanes/EtOAc/AcOH 60:40:1) provided the title compound (708 mg, 47% yield) as colorless oil. $^1$H-NMR (CDCl$_3$, 200.15 MHz): 7.33–7.19 (m, 4H); 5.85 (bs, 1H); 5.62 (bs, 1H); 5.34–5.15 (m, 4H); 4.52 (bs, 2H); 2.49–2.41 (m, 2H); 2.05–1.93 (m, 3H); 1.72 (t, J=2.7 Hz, 1H); 1.38–1.22 (m, 1H).

EXAMPLE 11

(1S,2S,5R,6S)-2-Allyloxycarbonylamino-2-(2',6'-dichlorobenzyloxycarbonyl)-bicyclo[3.1.0]hexane-6-carboxylic acid

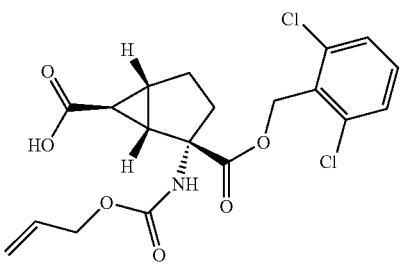

2,6-Dichlorobenzyl alcohol (2.4 g, 13.9 mmol) was reacted with the allyl-oxazolidinone (1.3 g, 4.6 mmol) following general procedure 1. Silica gel chromatography (hexane/EtOAc/AcOH 75:25:1) provided the title compound (705 mg, 37% yield) as a white solid. $^1$H-NMR (CDCl$_3$, 200.15 MHz): 7.36–7.19 (m, 3H); 5.92–5.76 (m, 1H); 5.44 (bs, 1H); 5.31–5.15 (m, 2H); 4.52 (dt, J=5.6, 1.6 Hz, 2H); 2.49 (dd, J=6.2, 2.7 Hz, 1H); 2.40 (m, 1H); 2.18–1.88 (m, 3H); 1.68 (t, J=3.0 Hz, 1H); 1.35–1.19 (m, 1H).

EXAMPLE 12

(1S,2S,5R,6S)2-Allyloxycarbonylamino-bicyclo[3.1.0]hexane-2,6-dicarboxylic acid 2-thiophen-2'-yl methyl ester

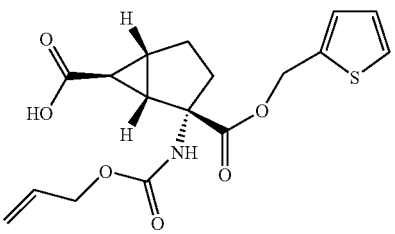

The title compound was prepared from 2-thiophenemethanol following the general procedure 1. (yield 35%)
$^1$H-NMR (CDCl$_3$, 200.15 MHz): 9.10–9.10 (m, 1H); 7.29 (dd, J=5.1, 1.1 Hz, 1H); 7.06 (d, J=2.6 Hz, 1H); 6.95 (dd, J=5.1, 3.7 Hz, 1H); 5.90–5.76 (m, 1H); 5.46–5.14 (m, 5H); 4.49 (d, J=5.5 Hz, 2H); 2.48–2.30 (m, 2H); 2.14–1.88 (m, 3H); 1.68 (t, J=2.6 Hz, 1H); 1.33–1.17 (m, 1H).

EXAMPLE 13

(1S,2S,5R,6S)2-Allyloxycarbonylamino-bicyclo[3.1.0]hexane-2,6-dicarboxylic acid 6-(2',4',6'-trimethyl) benzyl ester

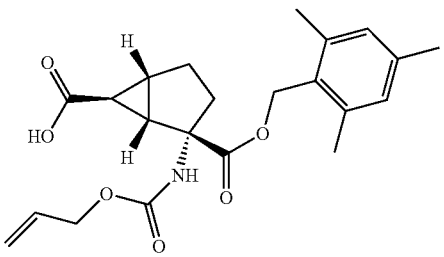

The title compound was prepared from 2,4,6-trimethyl-benzyl alcohol following the general procedure 1. (yield 78%).
$^1$H-NMR (CDCl$_3$, 200.15 MHz): 10.40 (br s, 1H); 6.83 (s, 2H); 5.80–5.72 (m, 1H); 5.53–5.42 (m, 1H); 5.27–5.11 (m, 4H); 4.44 (d, J=5.1 Hz, 2H); 2.44–2.36 (m, 2H); 2.30 (s, 6H); 2.24 (s, 3H); 2.10–1.93 (m, 3H); 1.66 (t, J=2.9 Hz, 1H); 1.31–1.15 (m, 1H).

EXAMPLE 14

(1S,2S,5R,6S)2-Allyloxycarbonylamino-bicyclo[3.1.0]hexane-2,6-dicarboxylic acid 6-(3',5'-dichloro)benzyl ester

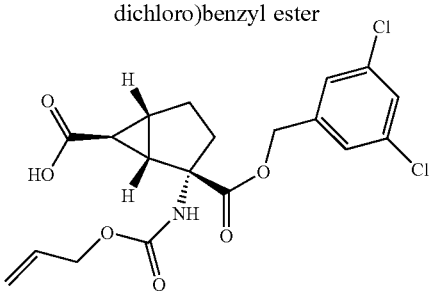

The title compound was prepared from 3,5-dichlorobenzyl alcohol following the general procedure 1. (yield 35%).

$^1$H-NMR (CDCl$_{3-200.15}$ MHz): 10.5–8.5 (br s, 1H); 7.29 (d, J=1.8 Hz, 1H); 7.19 (d, J=1.8 Hz, 2H); 5.91–5.81 (m, 1H); 5.52 (s, 1H); 5.31–5.09 (m, 4H); 4.52 (d, J=5.1 Hz, 2H); 2.48–2.37 (m, 2H); 2.13–1.96 (m, 3H); 1.70 (t, J=2.9 Hz, 1H); 1.35–1.18 (m, 1H).

GENERAL PROCEDURE 2

General Procedure for Esterification of (1S,2S,5R,6S)-2-Allyloxycarbonylamino-bicyclo[3.1.0]hexane-2,6-dicarboxylic acid 6-allyl ester with a Halide (1S,2S,5R,6S)-2-Allyloxycarbonylamino-bicyclo[3.1.0]hexane-2,6-dicarboxylic acid 6-allyl ester (1.0 equiv) was dissolved in dry dimethylformamide (0.5 M solution) and potassium carbonate (1.0 equiv) was added at room temperature under nitrogen. After 5 min, the corresponding halide (1.0 equiv) and sodium iodide (1.0 equiv) were added. The reaction mixture was stirred at room temperature overnight. Water was added and the aqueous phase was extracted twice with ethyl acetate. The combined organic phase was washed with cold water, dried over magnesium sulfate and concentrated at vacuum. The crude mixture was purified by silica gel chromatography.

EXAMPLE 15

(1S,2S,5R,6S)-2-Allyloxy carbonyl Amino bicyclo[3.1.0]hexane-2,6-dicarboxylic acid 6-allyl ester 2-(2'-methyl)benzyl ester

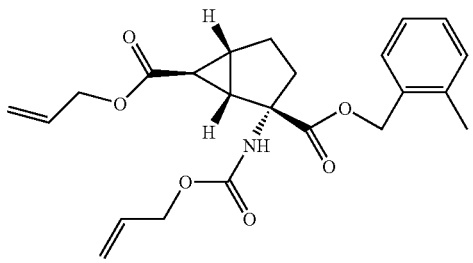

The title compound was prepared from 2-methylbenzyl bromide following the General Procedure 2. Chromatography solvent: (Hexane/Ethyl Acetate 1/1)

Yield: 64% (Oil)

$^1$H-NMR (CDCl$_3$): 7.3–7.1 (m, 4H); 5.99–5.80 (m, 2H); 5.34 (q, 1H, J=1.5 Hz); 5.26 (m, 1H); 5.21 (m, 2H); 5.19 (s, 2H); 4.54 (m, 4H); 2.50 (m, 1H); 2.40 (dd, 1H, J=2.8 and 6.4 Hz); 2.34 (s, 3H); 2.17–1.80 (m, 3H); 1.75 (t, 1H, J=2.9 Hz) and 1.25 (m, 1H).

EXAMPLE 16

(1S,2S,5R,6R)-2-Allyloxy carbonylamino bicyclo[3.1.0]hexane-2,6-dicarboxylic acid-6-allyl ester-2-(3',5'-dimethyl)benzyl ester

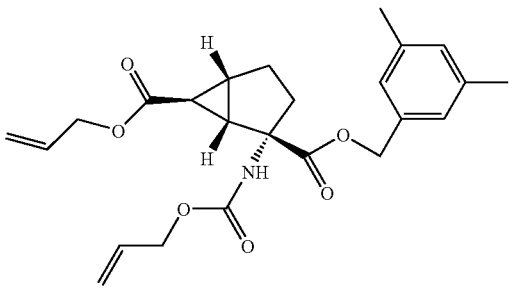

The title compound was prepared from 3,5-dimethylbenzyl bromide following General Procedure 2. Chromatography solvent (hexanes/ethyl acetate 4/1)

Yield: 83% (Oil)

$^1$H-NMR (CDCl$_3$): 6.98 (m, 3H); 5.97–5.80 (m, 2H); 5.36–5.10 (m, 4H); 5.11 (s, 2H); 4.56 (m, 4H); 2.50 (m, 1H); 2.42 (dd, 1H, J=2.7 and 6.2 Hz); 2.31 (s, 6H); 2.25–1.82 (m, 3H); 1.75 (t, 1H, J=2.9 Hz) and 1.25 (m, 1H) ppm.

EXAMPLE 17

2-Allyloxycarbonylamino-bicyclo[3.1.0]hexane-2,6-dicarboxylic acid 6-allyl ester 2-(3'-phenoxy)benzyl ester

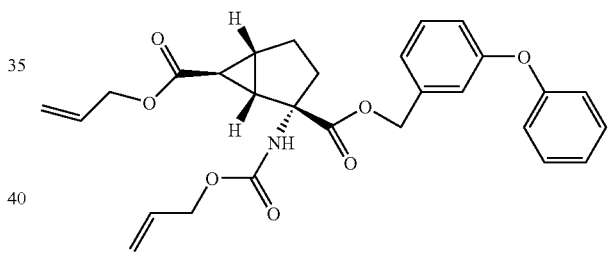

The title compound was prepared from 3-phenoxybenzyl chloride following general procedure 2.

Yield: 53% Chromatography solvent (Hexane/Ethyl Acetate 1/3)

$^1$H-NMR (CDCl$_3$): 7.34–7.27 (m, 3H); 7.14–6.94 (m, 6H); 5.86 (m, 2H); 5.38–5.15 (m, 4H); 4.53 (dd, 4H, J=3.6 and 9.0 Hz); 2.46–2.38 (m, 2H); 2.09–1.93 (m, 3H), 1.75 (t, 1H, J=2.9 Hz) and 1.25 (m, 1H) ppm.

EXAMPLE 18

(1S,2S,5R,6S)-6-Allyl, 2-(4'-acetoxybenzyl) 2-allyloxycarbonylamino-bicyclo[3.1.0]hexane-2,6-dicarboxylate

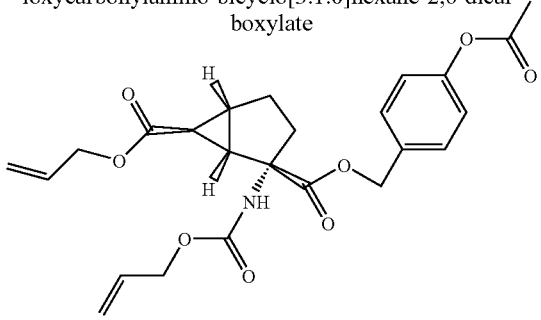

(1S,2S,5R,6S)-2-Allyloxycarbonylamino-bicyclo[3.1.0]
hexane-2,6-dicarboxylic acid 6-allyl ester (0.9 g, 2.9 mmol)
was reacted with cesium carbonate (995 mg, 3.06 mmol),
sodium iodide (458 mg, 3.06 mmol) and acetic acid 4-chloromethyl-phenyl ester (564 mg, 3.0 mmol) following general procedure 2. Silica gel chromatography of the crude
(hexanes/EtOAc 4:1 to hexanes/EtOAc 2:1) provided the
title compound (868 mg, 65% yield) as a colorless oil.
$^1$H-NMR (CDCl$_3$, 200.15 MHz): 7.34 and 7.07 (AA'BB'
system, 4H); 5.96–5.79 (m, 2H); 5.70 (bs, 1H); 5.35–5.14
(m, 6H); 4.56–4.48 (m, 4H); 2.44 (dd, J=5.9, 2.7 Hz, 2H);
2.28 (s, 3H); 2.07–1.89 (m, 3H); 1.75 (t, J=3.0 Hz, 1H);
1.37–1.26 (m, 1H).

GENERAL PROCEDURE 3

General Procedure for Esterification of (1S,2S,5R,
6S)-2-Allyloxycarbonylamino-bicyclo[3.1.0]hexane-
2,6-dicarboxylic acid 6-allyl ester with an Alcohol (1S,2S,5R,6S)-2-Allyloxycarbonylamino-bicyclo[3.1.0]
hexane-2,6-dicarboxylic acid 6-allyl ester (1.0 equiv) was
dissolved in dry dichloromethane (0.1 M solution). The
corresponding alcohol (1.2 equiv), N-ethyl-N'-dimethylaminopropylcarbodiimide (1.2 equiv) and dimethylaminopyridine (0.1 equiv) were added under nitrogen. The reaction
mixture was stirred overnight at room temperature, then
hydrolyzed by addition of water and diluted with methylene
chloride (10 mL/mmol). The aqueous layer was extracted
with methylene chloride (5 mL/mmol) and the combined
organic layers were washed twice with 1 N hydrochloric
acid (10 mL/mmol), water and brine (5 ml/mmol each).
After drying over sodium sulfate and evaporation in vacuum
the crude residue was purified by silica gel chromatography.

EXAMPLE 19

2-Allyloxycarbonylamino-bicyclo[3.1.0]hexane-2,6-
dicarboxylic acid 6-allyl ester 2-indan-5'-yl ester

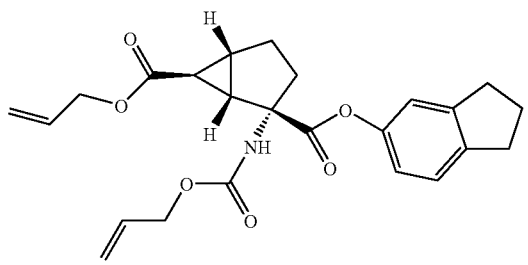

The title compound was prepared from 5-hydroxyindane
following general procedure 3.
Yield: 66% Chromatography solvent (Hexane/Ethyl
Acetate 8/1)
$^1$H-NMR (CDCl$_3$): 7.18 (d,1H, J=8.0 Hz); 6.94 (bs, 1H);
6.83 (bd, 1H, J=8.0 Hz); 5.90 (m, 2H); 5.78 (bs, 1H); 5.35
(m, 1H); 5.22 (m, 3H); 4.58 (dd, 4H, J=1.2 and 5.8 Hz); 2.87
(q, 4H, J=7.4 Hz); 2.63 (m, 1H); 2.58 (dd, 1H, J=2.8 and 6.2
Hz); 2.31–1.99 (m, 4H); 1.8 (t, 1H, J=2.8 Hz) and 1.38–1.21
(m, 2H) ppm.
$^{13}$C-NMR (CDCl$_3$): 172.3; 172.2 (2CO$_2$); 156.2 (NCOO);
149.8; 146.1; 142.2; 132.9; 132.4 (2CH=CH$_2$); 125.1;
119.3; 118.9; 118.3 (2CH=CH$_2$); 117.8; 67.3 (C-2); 66.3
(2CO$_2$); 65.9; 35.1; 33.3; 32.9; 32.7; 28.8; 27.2; 26.2 and
21.7 ppm.

EXAMPLE 20

(1S,2S,5R,6S)-2-Allyloxycarbonylamino-bicyclo
[3.1.0hexane-2,6-dicarboxylic acid 6-allyl ester,
2-(2'-phenyl)benzyl ester

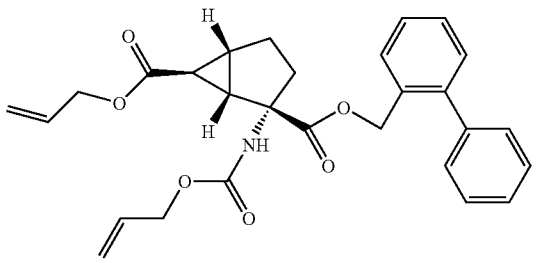

The title compound was prepared from 2-phenylbenzyl
alcohol following general procedure 3.
90% Yield. Colorless syrup.
$[\alpha]_D^{25}$=−1.50° (c=3.0, CHCl$_3$).
$^1$H NMR (CDCl$_3$) δ: 7.51–7.28 (m, 9H), 5.97–5.80 (m,
2H), 5.71 (brs, 1H), 5.35–5.05 (m, 4H), 5.14 (brs, 2H),
4.56–4.49 (m, 4H), 2.43–2.35 (m, 2H), 2.15–1.86 (m, 3H),
1.76 (t, 1H, J=2.8 Hz), 1.36–1.20 (m, 1H).
$^{13}$C NMR (CDCl$_3$) δ: 172.2, 171.8, 155.5, 142.1, 140.0,
132.6, 131.9, 130.0, 129.3, 129.0, 128.9, 128.9, 128.2,
128.1, 127.4, 127.2, 118.3, 117.6, 66.6, 65.6, 65.4, 65.2,
34.7, 32.4, 28.4, 26.7, 21.1.

EXAMPLE 21

(1S,2S,5R,6S)-2-Allyloxycarbonylamino-bicyclo
[3.1.0]hexane-2,6-dicarboxylic acid 6-allyl ester,
2-(3'-fluoro)benzyl ester

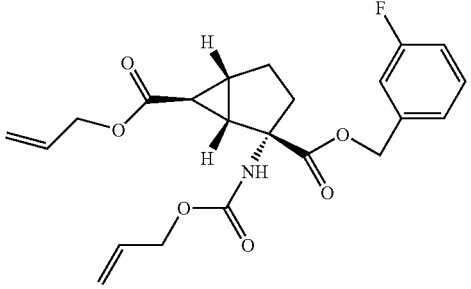

The title compound was prepared from 3-fluorobenzyl
alcohol following general procedure 3.
93% Yield. Colorless syrup.
$[\alpha]_D^{25}$=−13.0° (c=1.0, CHCl$_3$).
$^1$H NMR (CDCl$_3$) δ: 7.29 (m, 1H), 7.13–7.01 (m, 3H),
5.86 (m, 2H), 5.45 (brs, 1H), 5.35–5.16 (m, 4H), 5.17 (brs,
2H), 4.57–4.50 (m, 4H), 2.42 (m, 2H), 2.11–1.92 (m, 3H),
1.77 (t, 1H, J=2.7 Hz), 1.33–1.20 (m, 1H).
$^{13}$C NMR (CDCl$_3$) δ: 172.3, 171.7, 162.3 (d, J$_{C-F}$=240
Hz), 155.5, 137.9 (d, J$_{C-F}$=7.7 Hz), 132.3, 131.9, 130.0

($J_{C-F}$=8.1 Hz), 123.3 ($J_{C-P}$=2.4 Hz), 118.2 ($J_{C-F}$=29.5 Hz), 115.2, 114.9, 66.7, 66.4, 65.8, 65.4, 34.7, 32.5, 28.3, 26.8, 21.2.

EXAMPLE 22

(1S,2S,5R,6S)-2-Allyloxycarbonylamino-bicyclo[3.1.0]hexane-2,6-dicarboxylic acid 6-allyl ester, 2-(2',5'-dimethyl) benzyl ester

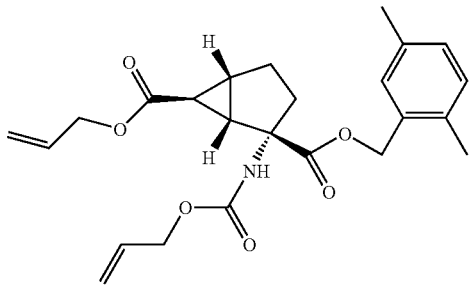

The title compound was prepared from 2,5-dimethylbenzyl alcohol following general procedure 3.
95% Yield. Colorless syrup.
$[\alpha]_D^{25}$=−1.67° (c=2.70, CHCl$_3$).
$^1$H NMR (CDCl$_3$) δ: 7.17–7.02 (m, 3H), 5.92–5.83 (m, 2H), 5.35–5.20 (m, 4H), 5.16 (brs, 2H), 4.56–4.48 (m, 4H), 2.43–2.38 (m, 2H), 2.31 (s, 3H), 2.29 (s, 3H), 2.07–1.96 (m, 3H), 1.75 (t, 1H, J=2.8 Hz), 1.29 (m, 1H).
$^{13}$C NMR (CDCl$_3$) δ: 172.4, 171.8, 155.5, 135.4, 133.8, 133.1, 132.3, 131.9, 130.2, 130.1, 129.2, 128.3, 118.4, 117.7, 66.0, 65.7, 65.4, 63.5, 34.8, 32.5, 28.4, 26.8, 21.3, 20.8, 18.2.

EXAMPLE 23

(1S,2S,5R,6S)-2-(2'-butoxybenzyl), 6-allyl 2-allyloxycarbonylamino-bicyclo[3.1.0]hexane-2,6-dicarboxylate

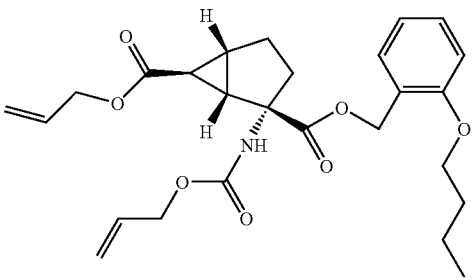

(1S,2S,5R,6S)-2-Allyloxycarbonylamino-bicyclo[3.1.0]hexane-2,6-dicarboxylic acid 6-allyl ester (1.3 g, 4.2 mmol) was reacted with (2-butoxy-phenyl)-methanol (827 mg, 4.6 mmol), N-ethyl-N'-dimethylaminopropylcarbodiimide (879 mg, 4.6 mmol) and dimethylaminopyridine (51 mg, 0.4 mmol) following general procedure 3. Silica gel chromatography (hexanes/EtOAc 6:1 to 4:1) provided the title compound (1.2 g, 61% yield) as a colorless oil.
$^1$H-NMR (CDCl$_3$, 200.15 MHz): 7.32–7.22 (m, 2H); 6.95–6.84 (m, 2H); 6.00–5.75 (m, 2H); 5.49 (bs, 1H); 5.35–5.14 (m, 6H); 4.57–4.50 (m, 4H); 3.98 (t, J=6.5 Hz, 2H); 2.51 (m, 1H); 2.44 (dd, J=6.2, 2.4 Hz, 1H); 2.24–1.70 (m, 7H); 1.59–1.40 (m, 2H); 1.38–1.21 (m, 1H); 0.97 (t, J=7.3 Hz, 3H).

EXAMPLE 24

(1S,2S,5R,6R)-2-Allyloxycarbonylamino bicyclo[3.1.0]hexane-2,6-dicarboxylic acid-6-allyl ester-2-(3',5'-dimethyl)benzyl ester

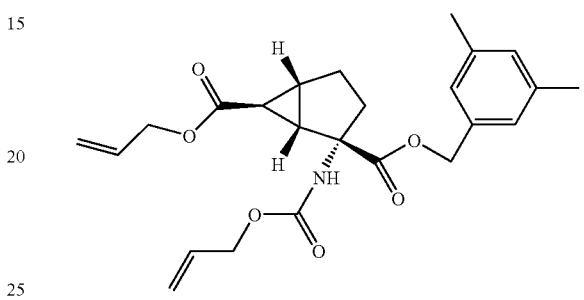

The title compound was prepared from 3,5-dimethylbenzyl alcohol following general procedure 3. Chromatograghy solvent (hexanes/ethyl acetate 4/1)
Yield: 83% (Oil)
$^1$H-NMR (CDCl$_3$): 6.98 (m, 3H); 5.97–5.80 (m, 2H) 5.36–5.10 (m, 4H) 5.11 (s, 2H); 4.56 (m, 4H); 2.50 (m, 1H); 2.42 (dd, 1H, J=2.7 and 6.2 Hz); 2.31 (s, 6H); 2.25–1.82 (m, 3H); 1.75 (t, 1H, J=2.9 Hz) and 1.25 (m, 1H) ppm.

EXAMPLE 25

(1S,2S,5R,6S)-6-Allyl, 2-(2',3'-difluorobenzyl)-2-allyloxycarbonylamino-bicyclo[3.1.0]hexane-2,6-dicarboxylate

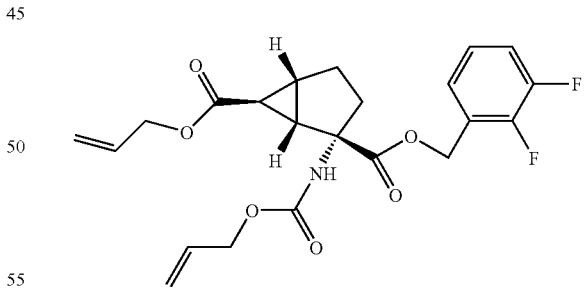

(1S,2S,5R,6S)-2-Allyloxycarbonylamino-bicyclo[3.1.0]hexane-2,6-dicarboxylic acid 6-allyl ester (0.9 g, 2.9 mmol) was reacted with 2,3-difluorobenzyl alcohol (0.36 mL, 3.2 mmol), N-ethyl-N'-dimethylaminopropylcarbodiimide (607 mg, 3.2 mmol) and dimethylaminopyridine (35 mg, 0.3 mmol) following general procedure 3. The crude material was purified by silica gel chromatography (hexanes/EtOAc 4:1) to provide the title compound (685 mg, 55% yield) as a colorless oil.

¹H-NMR (CDCl₃, 200.15 MHz): 7.20–7.09 (m, 3H); 6.02–5.78 (m, 2H); 5.47 (bs, 1H); 5.37–5.18 (m, 6H); 4.59–4.51 (m, 4H); 2.50–2.43 (m, 2H); 2.20–1.97 (m, 3H); 1.78 (t, J=2.9 Hz, 1H); 1.38–1.22 (m, 2H).

EXAMPLE 26

(1S,2S,5R,6S)-2-Allyloxycarbonylamino-bicyclo[3.1.0]hexane-2,6-dicarboxylic acid 6-allyl ester 2-(2',5'-difluoro)benzyl ester

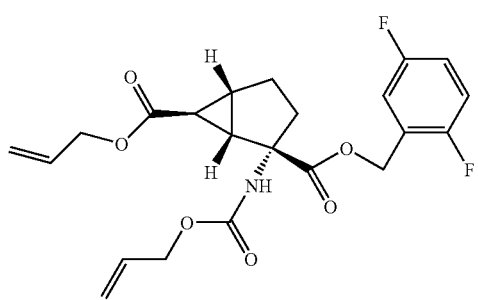

The title compound was prepared from 3,5-difluorobenzyl alcohol following general procedure 3.

65% yield, oil

¹H NMR (CDCl₃) ?: 7.17–6.93 (m, 3H), 5.85–6.00 (m, 2H), 5.39–5.13 (m, 4H), 4.58–4.49 (m, 4H), 2.55–2.36 (m, 2H), 2.20–1.91 (m, 3H), 1.82 (t, 1 H, J=3.0 Hz), 1.30 (m, 1H).

EXAMPLE 27

(1S,2S,5R,6S)2-Allyloxycarbonylamino-bicyclo[3.1.0]hexane-2,6-dicarboxylic acid 6-allyl ester 2-benzo[b]thiophen-2'-yl methyl ester

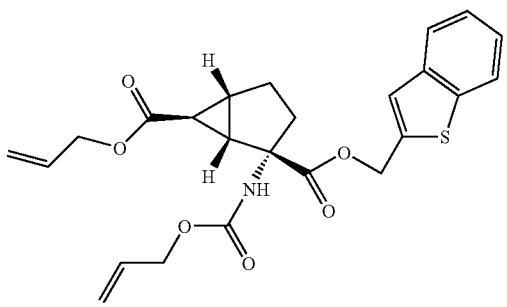

The title compound was prepared from 2-benzothiophenemethanol (example preparation 7) following general procedure 3.

Yield (75%).

¹H-NMR (CDCl₃, 200.15 MHz): 7.83–7.71 (m, 2H); 7.36–7.22 (m, 3H); 5.97–5.80 (m, 2H); 5.43–5.12 (m, 7H); 4.57–4.50 (m, 4H); 2.53–2.42 (m, 2H); 2.21–1.94 (m, 3H); 1.76 (t, J=3.0 Hz, 1H); 1.37–1.20 (m, 1H)

EXAMPLE 28

(1S,2S,5R,6S) 2-tert-Butoxycarbonylaminobicyclo[3.1.0]-hexane-2,6-dicarboxylic acid 2-(2'-chloro)benzyl ester

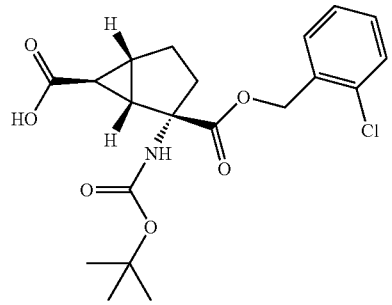

(1S,2S,5R,6S) 2-tert-Butoxycarbonylaminobicyclo[3.1.0]-hexane-2,6-dicarboxylic acid (1.0 equiv) was dissolved in dry dimethylformamide (0.5 M solution) and cesium carbonate (1.0 equiv) was added at room temperature under nitrogen. After 5 min., 2-chlorobenzyl bromide (1.0 equiv) and sodium iodide (1.0 equiv) were added. The reaction was stirred overnight at room temperature. Water was added and the aqueous phase was extracted with two portions of ethyl acetate. The combined organic phase was washed with cold water, dried over magnesium sulfate and concentrated to dryness. The crude product was purified by silica gel chromatography to provide the title compound as a colorless oil (yield 35%).

¹H NMR (Methanol-d₄): 7.54–7.29 (m, 4H), 5.26 (s, 2H), 2.44 (m, 1H), 2.00–1.90 (m, 4H), 1.63 (brs, 1H), 1.37 (m, 1H) ppm

GENERAL PROCEDURE 4

General Procedure for 2-Allyloxycarbonylamino-6-allyl Ester and 2-Allyoxycarbonyl-6-carboxylic acid Deprotection and Hydrochloride Formation The corresponding (1S,2S,5R,6S)-2-allyloxycarbonylamino-bicyclo[3.1.0]hexane-2,6-dicarboxylic acid 2-ester 6-allyl ester or (1S,2S,5R,6S)-2-allyloxycarbonylamino-bicyclo[3.1.0]hexane-2,6-dicarboxylic acid 2-ester was dissolved in dry dichloromethane (0.1 M solution) under nitrogen. 1,3-Dimethylbarbituric acid (1.5 equiv per allyl group) and tetrakis(triphenylphosphine)palladium(0) (0.015 equiv per allyl group) were added and the solution was heated at 35° C. for 2 h. After cooling to room temperature, the solvent was removed under vacuum and the resulting residue was dissolved in a solution of ethyl acetate saturated with hydrogen chloride gas and stirred for 2 h. In the case where a solid appeared, the reaction was filtered. The filtrated material was washed with ethyl acetate and ether, and dried to provide the product. In the case where a solid did not appear, the solvent was removed under vacuum, ethyl ether was added and the mixture was stirred overnight. The solid was filtered, washed thoroughly with ether and dried to provide the product.

EXAMPLE 29

(1S,2S,5R,6S)-2-Amino-bicyclo[3.1.0]hexane-2,6-dicarboxylic acid 2-(2',4'-dichloro)benzyl ester hydrochloride

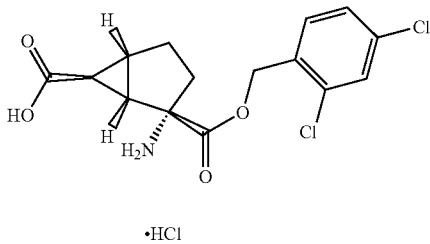

·HCl

The title compound was prepared following general procedure 4.

79% yield. Solid. m.p. 135–137° C.

IR (KBr) ν: 3500–2500 (br), 2960, 2887, 1747, 1699, 1591, 1570, 1506, 1477, 1441, 1371, 1334, 1263, 1190, 1105, 1057 cm$^{-1}$.

$^1$H NMR (CD$_3$OD) δ: 7.57 (d, 1H, J=2.0 Hz, C-3'), 7.55 (d, 1H, J=8.2 Hz, C-6'), 7.41 (dd, 1H, J=8.2, 2.0 Hz, C-5'), 5.41 (s, 2H, CO$_2$CH$_2$), 2.30–2.00 (m, 6H), 1.56 (m, 1H)

$^{13}$C NMR (CD$_3$OD) δ: 174.9 (CO$_2$H), 171.3 (CO$_2$CH$_2$), 136.9, 136.4, 133.6, 132.9, 130.7, 128.9 (Aromatics), 67.2 (C-2), 66.5 (CO$_2$CH$_2$), 34.0 (C-1), 31.6 (C-3), 30.1 (C-5), 28.0 (C-4), 22.5 (C-6).

MS (Electrospray): 344.0 (M$^+$+H)

EXAMPLE 30

(1S,2S,5R,6S)-2-Amino-bicyclo[3.1.0]hexane-2,6-dicarboxylic acid 2-(4'-butoxy)benzyl ester hydrochloride

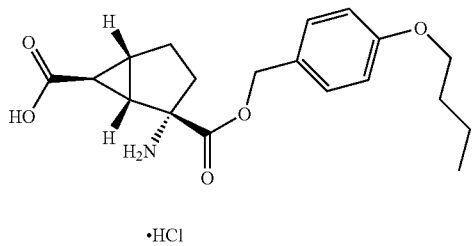

·HCl

The title compound was prepared following general procedure 4.

95% yield. Solid. 158–159° C.

IR (KBr) ν: 3500–2200 (br), 1749, 1699, 1612, 1583, 1574, 1527, 1514, 1444, 1393, 1369, 1346, 1305, 1260, 1199, 1109 cm$^{-1}$.

$^1$H NMR (CD$_3$OD) δ: 7.35 (d, 2H, J=8.6 Hz, C-2', C-6'), 6.92 (d, 2H, J=8.6 Hz, C-3', C-5'), 5.25 (AB system, 2H, J$_{gem}$=11.8 Hz, CO$_2$CH$_2$), 3.98 (t, 2H, J=6.4 Hz, OCH$_2$), 2.30–1.95 (m, 6H), 1.76 (qt, 2H, CH$_2$), 1.50 (st, 3H, CH$_2$CH$_3$, CH), 0.98 (t, 3H, CH$_3$).

$^{13}$C NMR (CD$_3$OD) δ: 174.9 (CO$_2$H), 171.4 (Co$_2$CH$_2$), 161.2, 131.7, 128.3, 115.7 (Aromatics), 69.7 (CH$_2$), 68.9 (CH$_2$), 67.2 (C-2), 34.0 (C-1), 32.6, 31.5 (C-3, CH$_2$), 30.1 (C-5), 28.0 (C-4), 22.4 (C-6), 20.4 (CH$_2$), 14.3 (CH$_3$).

MS (Electrospray): 348.1 (M$^+$+H).

EXAMPLE 31

(1S,2S,5R,6S)-2-Amino-bicyclo[3.1.0]hexane-2,6-dicarboxylic acid 2-(2'-fluoro)benzyl ester hydrochloride

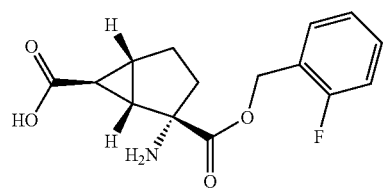

·HCl

The title compound was prepared following general procedure 4.

84% yield. Solid. MP>220° C. (dec).

IR (KBr) ν: 3300–2400, 1749, 1684, 1577, 1531, 1493, 1447, 1385, 1373, 1332, 1312, 1265, 1205 cm$^{-1}$.

$^1$H NMR (CD$_3$OD) δ: 7.64–7.38 (m, 2H, aromatics), 7.26–7.12 (m, 2H, aromatics), 5.41 (AB system, 2H, CO$_2$CH$_2$), 2.28–1.99 (m, 6H), 1.58 (m, 1H).

$^{13}$C NMR (CD$_3$OD) δ: 174.8 (CO$_2$H), 171.3 (CO$_2$CH$_2$), 162.7 (d, C-2', J=250 Hz), 132.5, 132.4 (2d, C-4', C-6'), 125.8 (d, J=5 Hz, C-5'), 123.5 (d, J=15 Hz, C-1'), 116.7 (d, J=20 Hz, C-3'), 67.3 (C-2), 63.8 (CO$_2$CH$_2$), 33.9 (C-1), 31.6 (C-3), 30.0 (C-5), 27.9 (C-4), 22.4 (C-6).

MS (Electrospray): 316.1 (M$^+$+Na).

EXAMPLE 32

(1S,2S,5R,6S)-2-Amino-bicyclo(3.1.0]hexane-2,6-dicarboxylic acid 2-(2'-trifluoromethyl)benzyl ester hydrochloride

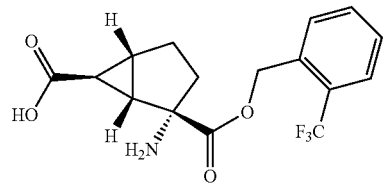

·HCl

The title compound was prepared following general procedure 4.

84% yield. Solid. MP>175° C. (dec).

IR (KBr) ν: 3500–2500, 3391, 2961, 1746, 1705, 1589, 1514, 1456, 1439, 1385, 1317, 1265, 1192, 1172, 1120, 908 cm$^{-1}$.

$^1$H NMR (CD$_3$OD) δ: 7.80–7.50 (m, 4H, aromatic), 5.52 (AB system, 2H, CO$_2$CH$_2$), 2.30–2.00 (m, 6H), 1.60 (m, 1H).

$^{13}$C NMR (CD$_3$OD) δ: 174.7 (CO$_2$H), 171.3 (CO$_2$CH$_2$), 134.2 (C-1'), 134.0, 132.7, 130.7 (aromatics), 129.9 (q, J=31 Hz, C-2'), 127.6 (q, J=5 Hz, C-3'), 125.8 (q, J=271 Hz, CF$_3$), 67.3 (C-2), 66.2 (CO$_2$CH$_2$), 33.9 (C-1), 31.6 (C-3) 30.0 (C-5), 27.9 (C-4), 22.5 (C-6).

MS (Electrospray): 366.1 (M$^+$+Na)

EXAMPLE 33

(1S,2S,5R,6S)-2-Amino-bicyclo[3.1.0]hexane-2,6-dicarboxylic acid 2-(2',5'-dichloro)benzyl ester hydrochloride

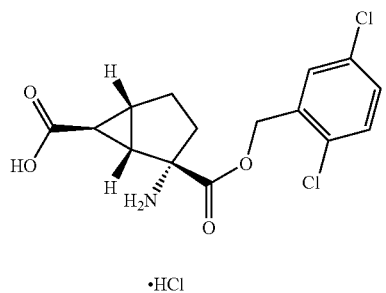

·HCl

The title compound was prepared following general procedure 4.

79% yield. Solid. m.p. 173–175° C.

IR (KBr) ν: 3300–2400, 2963, 1741, 1687, 1580, 1529, 1469, 1447, 1371, 1332, 1263, 1199, 1101 cm$^{-1}$.

$^1$H NMR (CD$_3$OD) δ: 7.58 (d, 1H, J=2.2 Hz, C-3'), 7.47 (s, 1H, C-6'), 7.44 (d, 1H, C-4'), 5.41 (s, 2H, CO$_2$CH$_2$), 2.33–2.01 (m, 6H), 1.57 (m, 1H).

$^{13}$C NMR (CD$_3$OD) : 174.7 (CO$_2$H), 171.2 (CO$_2$CH$_2$), 135.8, 134.3, 133.8, 132.4, 132.1, 131.7 (Aromatics), 67.3, 66.6 (C-2, CO$_2$CH$_2$), 34.0 (C-1), 31.6 (C-3), 30.1 (C-5), 28.0 (C-4), 22.5 (C-6).

MS (Electrospray): 344.0 (M$^+$+1).

EXAMPLE 34

(1S,2S,5R,6S)-2-Amino-bicyclo[3.1.0]hexane-2,6-dicarboxylic acid 2-(2'-bromo)benzyl ester hydrochloride

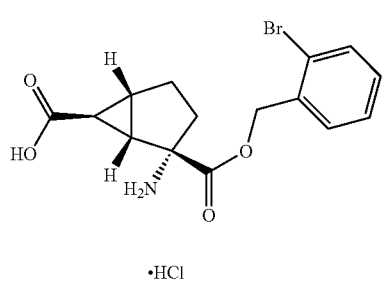

·HCl

The title compound was prepared following general procedure 4.

85% Yield. White solid. mp 190–191° C.

[α]$_D$$^{25}$=+2.20° (c=0.5, MeOH).

$^1$H NMR (Methanol-d$_4$) δ: 7.67 (dd, 1H, J=7.7, 1.3 Hz), 7.55 (dd, 1H, J=7.4, 1.7 Hz), 7.41 (td, 1H, J=7.4, 1.2 Hz), 7.31 (td, 1H, J=7.6, 1.9 Hz), 5.40 (AB system, 2H), 2.33–1.99 (m, 6H), 1.64–1.47 (m, 1H).

$^{13}$C NMR (Methanol-d$_4$) δ: 173.7, 170.3, 134.1, 133.2, 131.4, 131.0, 128.1, 123.2, 68.3, 66.2, 32.9, 30.5, 29.0, 26.9, 21.3.

MS (Electrospray): 353.02.

EXAMPLE 35

(1S,2S,5R,6S)-2-Amino-bicyclo[3.1.0]hexane-2,6-dicarboxylic acid 2-(3',5'-difluoro)benzyl ester hydrochloride

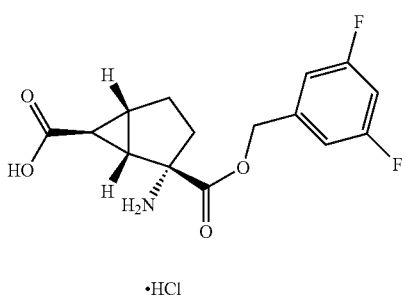

·HCl

The title compound was prepared following general procedure 4.

84% Yield. White solid. mp 98–99° C.

[α]$_D$$^{25}$=+4.88° (c=0.86, MeOH)

$^1$H NMR (Methanol-d$_4$) δ: 7.12–6.92 (m, 3H), 5.33 (brs, 2H), 2.34–2.02 (m, 6H), 1.67–1.61 (m, 1H).

$^{13}$C NMR (Methanol-d$_4$) δ: 173.5, 169.7, 163.3 (dd, J$_{C-F}$=245, 15 Hz), 139.3 (t, J$_{C-F}$=10 Hz), 110.7 (dd, J$_{C-F}$=15, 10 Hz), 103.4 (t, J$_{C-F}$=35 Hz), 66.6, 65.7, 32.4, 30.1, 28.5, 26.5, 21.0.

MS (Electrospray): 311.10.

EXAMPLE 36

(1S,2S,5R,6S)-2-Amino-2-(3'-chlorobenzyloxycarbonyl)-bicyclo[3.1.0]hexane-6-carboxylic acid

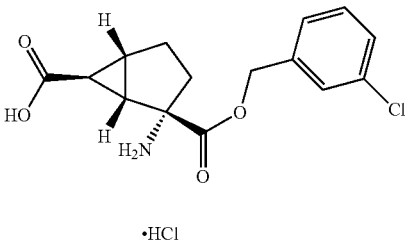

·HCl (1S,2S,5R,6S)-2-Allyloxycarbonylamino-2-(3'-chlorobenzyloxycarbonyl)-bicyclo[3.1.0]hexane-6-carboxylic acid (708 mg, 1.8 mmol) was reacted with dimethylbarbituric acid (421 mg, 2.7 mmol) and tetrakis triphenylphosphine palladium (0) (42 mg; 0.02 mmol) under general procedure 4. The title compound was obtained as a white solid (385 mg, 62% yield).

mp 122–123° C.

[α]$_D$$^{25}$+3° (c=1, MeOH).

$^1$H NMR (Methanol-d$_4$) δ: 7.49 (s, 1H); 7.41 (m, 3H); 5.34 (s, 2H); 2.32–2.00 (m, 6H); 1.67–1.49 (m, 1H).

$^{13}$C NMR (Methanol-d$_4$) δ: 173.1, 169.7, 137.2, 134.0, 129.9, 128.4, 128.0, 126.3, 67.2, 65.6, 32.8, 32.3, 30.0, 28.4, 26.4, 20.8.

I.R. (KBr): 3501, 2868, 1763, 1667.

MS (Electrospray)M$^+$+1: 310.

EXAMPLE 37

(1S,2S,5R,6S)-2-Amino-2-(2',6'-dichlorobenzyloxycarbonyl)-bicyclo[3.1.0]hexane-6-carboxylic acid hydrochloride

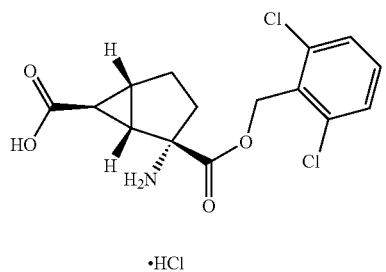

•HCl (1S,2S,5R,6S)-2-Allyloxycarbonylamino-2-(2',6'-dichlorobenzyloxycarbonyl-bicyclo[3.1.0]hexane-6-carboxylic acid (705 mg, 1.6 mmol) was reacted with dimethylbarbituric acid (380 mg, 2.5 mmol) and tetrakistriphenylphosphine palladium (0) (38 mg; 0.03 mmol) following general procedure 4. The title compound was obtained as a white solid (200 mg, 32% yield).

mp 149–152° C.

[α]$_D^{25}$=–3° (c=1, MeOH)

$^1$H NMR (Methanol-d$_4$) δ: 7.54–7.38 (m, 3H); 5.65 (s, 2H); 2.26–1.97 (m, 6H); 1.70–1.45 (m, 1H).

$^{13}$C NMR (Methanol-4)δ: 174.6, 171.2, 138.0, 132.8, 131.5, 129.9, 67.2, 64.2, 33.8, 31.5, 29.9, 27.8, 22.3.

I.R. (KBr): 3424, 2957, 1747, 1701, 1190.

MS (Electrospray)M$^+$+1: 344.

EXAMPLE 38

(1S,2S,5R,6S)2-Amino-bicyclo[3.1.0]hexane-2,6-dicarboxylic acid 6-(2',4',6'-trimethyl)benzyl ester hydrochloride

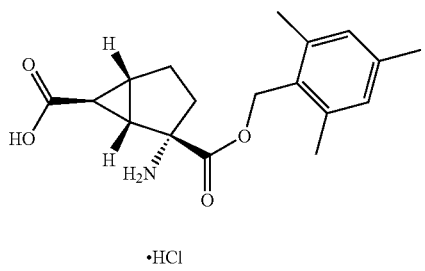

•HCl

The tile compound was prepared from 2-allyloxycarbonylamino-bicyclo[3.1.0]hexane-2,6-dicarboxylic acid 6-(2',4',6'-trimethyl) benzyl ester following general procedure 4. Yield (89%).

$^1$H-NMR (CD$_3$OD, 200.15 MHz): 6.90 (s, 2H); 5.43 (s, 2H); 2.39 (s, 6H); 2.25 (s, 3H); 2.19–1.96 (m, 6H); 1.61–1.45 (m, 1H).

$^{13}$C-NMR (CD$_3$OD, 50 MHz): 174.7, 171.5, 140.2, 139.5, 130.1, 129.3, 67.2, 64.5, 33.9, 31.5, 29.9, 27.9, 22.3, 21.1, 19.6.

EXAMPLE 39

(1S,2S,5R,6S)2-Amino-bicyclo[3.1.0]hexane-2,6-dicarboxylic acid 2-thiophen-2'-yl methyl ester hydrochloride

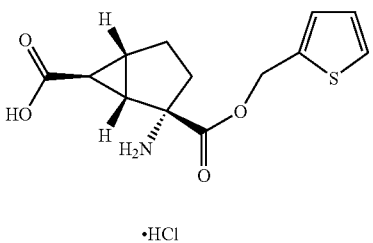

•HCl

The tile compound was prepared from 2-Allyloxycarbonylamino-bicyclo[3.1.0]hexane-2,6-dicarboxylic acid 2-thiophen-2'-yl methyl ester following general procedure 4. Yield (62%).

$^1$H-NMR (CD$_3$OD, 200.15 MHz): 7.49 (dd, J=5.1, 1.1 Hz, 1H); 7.22 (d, J=3.5 Hz, 1H); 7.03 (dd, J=5.1, 3.5 Hz, 1H); 5.52 (d, J=3.8 Hz, 2H); 2.22–1.96 (m, 6H); 1.58–1.47 (m, 1H).

EXAMPLE 40

(1S,2S,5R,6S)-2-Amino-bicyclo[3.1.0]hexane-2,6-dicarboxylic acid 2-(2'-phenyl)benzyl ester hydrochloride

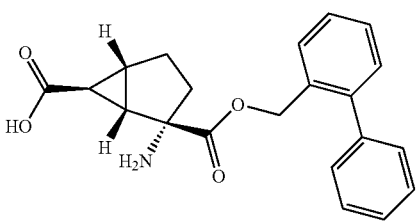

•HCl

The tile compound was prepared following general procedure 4.

90% Yield. White solid.

[α]$_D^{25}$=+10.9° (c=1.0, MeOH).

$^1$H NMR (Methanol-d$_4$) δ: 7.58–7.30 (m, 9H), 5.27 (AB system, 2H), 2.12–1.98 (m, 6H), 1.54–1.48 (m, 1H).

$^{13}$C NMR (Methanol-d$_4$) δ: 174.0, 170.3, 143.2, 140.7, 132.2, 130.4, 130.3, 129.3, 129.2, 128.6, 127.9, 127.7, 67.0, 66.1, 32.9, 30.4, 29.0, 26.9, 21.5.

EXAMPLE 41

(1S,2S,5R,6S)-2-Amino-bicyclo[3.1.0]hexane-2,6-dicarboxylic acid 2-(2',5'-dimethyl)benzyl ester hydrochloride

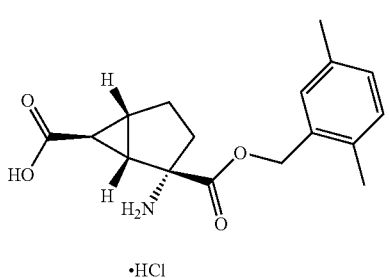

·HCl

The tile compound was prepared following general procedure 4.

56% Yield. White solid. mp 70° C., dec.

[α]$_D^{25}$=+9.30° (c=1.0, MeOH).

$^1$H NMR (Methanol-d$_4$) δ: 7.19 (brs, 1H), 7.10 (AB system, 2H), 5.33 (brs, 2H), 2.35 (s, 3H), 2.30 (s, 3H), 2.26–1.99 (m, 6H), 1.59–1.50 (m, 1H).

$^{13}$C NMR (Methanol-d$_4$) δ: 173.2, 169.8, 135.3, 133.9, 132.5, 130.2, 130.0, 129.3, 66.7, 65.7, 32.4, 30.0, 28.5, 26.4, 20.9, 19.4, 17.0.

EXAMPLE 42

(1S,2S,5R,6S)-2-Amino-bicyclo[3.1.0]hexane-2,6-dicarboxylic acid 2-(2'-methyl)benzyl ester hydrochloride

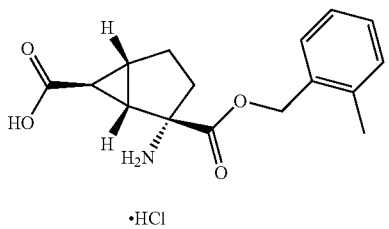

·HCl

The tile compound was prepared following general procedure 4.

Yield: 89% (Solid)

$^1$H-NMR (Methanol-d$_4$): 7.38 (d, 1H, J=6.9 Hz); 7.30 (m, 3H); 5.34 (s, 2H); 2.42 (s, 3H); 2.31–2.00 (m, 6H) and 1.52 (m, 1H) ppm.

$^{13}$C-NMR (Methanol-d$_4$): 172.6 (CO$_2$H); 169.2 (CO$_2$CH$_2$); 136.5; 132.1; 129.5; 128.9; 128.2; 125.1 (Aromatics); 66.0 (CO$_2$CH$_2$); 65.0 (C-2).; 31.8; 29.4; 27.9; 25.8; 20.2 and 16.9 ppm.

EXAMPLE 43

(1S,2S,5R,6R)-2-Amino-bicyclo[3.1.0]hexane-2,6-dicarboxylic acid 6-(3',5'-dimethyl)benzyl ester hydrochloride

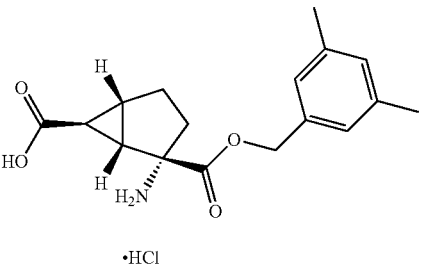

·HCl

The tile compound was prepared following general procedure 4.

Yield: 51% (Solid)

$^1$H-NMR (Methanol-d$_4$): 7.03 (bs, 3H); 5.25 (bs, 2H); 2.31 (s, 6H); 2.19–2.08 (m, 5H); 1.97 (m, 1H) and 1.48 (m, 1H) ppm.

$^{13}$C-NMR (Methanol-d$_4$): 175.1 (CO$_2$H); 172.8 (CO$_2$CH$_2$); 140.0; 137.1; 127.7 (Aromatics); 70.1 (CO$_2$CH$_2$); 67.5 (C-2); 34.3; 31.8; 30.4; 28.3; 22.7 and 21.7 ppm.

EXAMPLE 44

2-Amino-bicyclo[3.1.0]hexane-2,6-dicarboxylic acid 2-indan-5'-yl ester hydrochloride

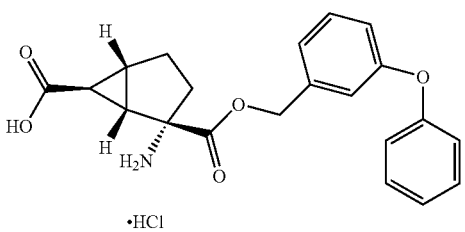

·HCl

The tile compound was prepared following general procedure 4.

Yield: 41% (Solid)

$^1$H-NMR (Methanol-d$_4$): 7.26 (d, 1H, J=8.2 Hz); 7.05 (s, 1H); 6.93 (dd, 1H, J=2.3 and 8.0 Hz); 2.91 (q, 4H, J=7.2 Hz); 2.44 (m, 3H); 2.23–2.09 (m, 5H) and 1.68 (m, 1H) ppm.

$^{13}$C-NMR (Methanol-d$_4$): 173.1 (CO$_2$H); 169.0 (COO); 148.6; 145.8; 142.5; 124.5; 118.2; 116.5 (Aromatics); 65.8 (C-2); 32.3; 31.7; 30.2; 28.5; 26.4; 25.4 and 20.9 ppm.

EXAMPLE 45

2-Amino-bicyclo[3.1.0]hexane-2,6-dicarboxylic acid 2-(3'-phenoxy)benzyl ester hydrochloride The tile compound was prepared following general procedure 4.

Yield: 51% (Solid)

$^1$H-NMR (Methanol-d$_4$): 7.37 (m, 3H); 7.15 (d, 2H, J=7.2 Hz); 7.01 (d, 4H, J=8.6 Hz); 5.30 (s, 2H); 2.23–1.97 (m, 6H) and 1.52 (m, 1H) ppm.

$^{13}$C-NMR (Methanol-d$_4$): 173.1 (CO$_2$H); 169.7 (COO); 157.9; 156.7; 136.9; 134.6; 129.8; 129.6; 123.4; 122.4; 118.8; 118.4; 117.3 (Aromatics); 67.5 (CH$_2$); 65.6 (C-2); 32.3; 30.0; 28.4; 26.4 and 20.8 ppm.

EXAMPLE 46

(1S,2S,5R,6S)-2-Amino-2-(4'-acetoxybenzyloxycarbonyl)-bicyclo[3.1.0]hexane-6-carboxylic acid hydrochloride

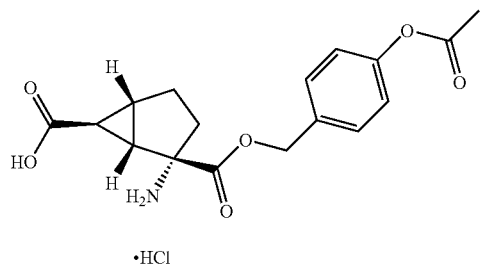

•HCl (1S,2S,5R,6S)-6-Allyl-2-(4'-acetoxybenzyl)-2-allyloxycarbonylamino-bicyclo[3.1.0]hexane-2,6-dicarboxylate (868 mg, 1.9 mmol) was reacted with dimethylbarbituric acid (661 mg, 4.2 mmol) and tetrakis triphenylphosphine palladium (0) (44 mg; 0.04 mmol) following general procedure 4 to provide the title compound (230 mg, 33% yield two steps) as a yellow solid.

mp 126–128° C.

$[\alpha]_D^{25}$=+4° (c=1, MeOH).

$^1$H NMR (Methanol-d$_4$) δ: 7.48 and 7.15 (AA'BB' system, 2H); 5.35 and 5.29 (AB system, J=12.4 Hz, 2H); 2.30–1.98 (m, 9 H); 1.63–1.44 (m, 1H).

I.R. (KBr): 3498, 1760, 1697.

MS (Electrospray)M$^+$+1: 334.

EXAMPLE 47

(1S,2S,5R,6S) 2-aminobicyclo[3.1.0]-hexane-2,6-dicarboxylic acid 2-(2'-chloro)benzyl ester hydrochloride

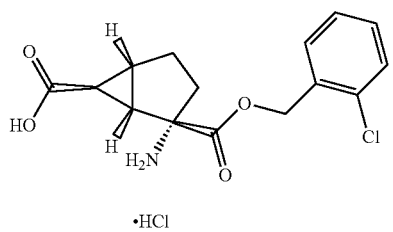

•HCl (1S,2S,5R,6S) 2-tert-Butoxycarbonylaminobicyclo[3.1.0]-hexane-2,6-dicarboxylic acid 2-(2'-chloro)benzyl ester was dissolved in ethyl acetate previously saturated with hydrogen chloride gas. The resulting mixture was stirred overnight at room temperature. The reaction was evaporated to dryness. The resulting residue was dissolved in a minimum volume of ethyl acetate. The solution was triturated with ethyl ether and the resulting precipitate was collected, washed with ethyl ether and dried to provide the title compound as a white solid (yield 90%).

$^1$H NMR (Methanol-d$_4$): 7.56–7.35 (m, 4H), 5.43 (AB system, 2H), 2.26–1.49 (m, 6H), 1.55–1.49 (m, 1H) ppm $^{13}$C NMR (Methanol-d4): 175.0, 170.0, 134.1, 132.5, 131.3, 130.8, 129.9, 127.5, 66.1, 64.1, 32.9, 30.5, 29.0, 26.9, 21.4 ppm MS (electrospray): 310.0

GENERAL PROCEDURE 5

General Procedure for 2-Allyloxycarbonylamino-6-allyl Ester and 2-Allyoxycarbonyl-6-carboxylic acid Deprotection and Zwitterion Formation The corresponding (1S,2S,5R,6S)-2-allyloxycarbonylamino-bicyclo[3.1.0]hexane-2,6-dicarboxylic acid 2-ester 6-allyl ester or (1S,2S,5R,6S)-2-allyloxycarbonylamino-bicyclo[3.1.0]hexane-2,6-dicarboxylic acid 2-ester was dissolved in dry dichloromethane (0.1 M solution) under nitrogen. 1,3-Dimethylbarbituric acid (0.5 equiv per allyl group) and tetrakis(triphenylphosphine)palladium(0) (0.02 equiv per allyl group) were added and the solution was heated at 35° C. for 2 h. The reaction was cooled to room temperature. In the case where a solid appeared, the reaction was filtered. The filtrated material was washed with dichloromethane, ethyl acetate and ether, and dried to provide the product. In the case where a solid did not appear, the solvent was removed under vacuum and a large amount of ethyl ether was added. After stirring for 30 min., the solid was filtered and washed with ether and ethyl acetate, and dried to provide the product.

EXAMPLE 48

(1S,2S,5R,6S)-2-Amino-bicyclo[3.1.0]hexane-2,6-dicarboxylic acid 2-(2'-methoxy)benzyl ester

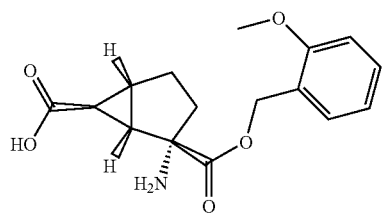

The tile compound was prepared following general procedure 5.

84% Yield. White solid. mp 195° C., dec.

$[\alpha]_D^{25}$=–11.6° (c=1.0, MeOH).

$^1$H NMR (Methanol-d$_4$) δ: 7.39–7.31 (m, 2H), 7.03–6.91 (m, 2H), 5.31 (AB system, 2H), 3.86 (s, 3H), 2.14–1.91 (m, 5H), 1.68 (t, 1H, J=2.8 Hz), 1.55–1.32 (m, 1H).

$^{13}$C NMR (Methanol-d$_4$) δ: 177.0, 171.2, 129.9, 129.7, 127.6, 123.0, 120.0, 110.3, 65.8, 63.5, 54.5, 32.4, 30.9, 27.3, 26.5, 23.5.

EXAMPLE 49

(1S,2S,5R,6S)-2-Amino-2-benzhydryloxycarbonyl-bicyclo[3.1.0]hexane-6-carboxylic acid

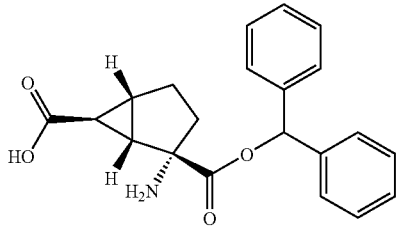

(1S,2S,5R,6S)-2-Allyloxycarbonylamino-2-benzydryloxycarbonyl-bicyclo[3.1.0]hexane-6-carboxylic acid (430 mg, 1.2 mmol) was reacted with dimethylbarbituric acid (96 mg, 0.6 mmol) and tetrakis triphenylphosphine palladium (0) (28 mg; 0.02 mmol) following general procedure 5 to provide the title compound as a white solid (250 mg, 58% yield). $^1$H-NMR (D$_2$O+Py-d$_5$, 200.15 MHz): 6.83–6.80 (m, 10H) 6.28 (s, 1H); 1.80 (m, 1H); 1.54–1.43 (m, 5H); 1.21–1.13 (m, 1H). $^{13}$C-NMR (DMSO-d$_6$+TFA-d, 50 MHz): 173.0, 169.4, 140.1, 140.0, 129.1 (2C), 129.0 (2C), 128.5, 128.4, 126.8 (2C), 126.6 (2C), 79.1, 65.5, 32.7, 30.3, 28.2, 27.1, 21.2.

EXAMPLE 50

(1S,2S,5R,6S)2-Amino-bicyclo[3.1.0]hexane-2,6-dicarboxylic acid 2-thiophen-2'-yl methyl ester

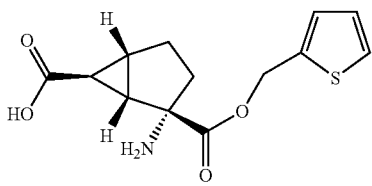

The title compound was prepared from 2-allyloxycarbonylamino-bicyclo[3.1.0]hexane-2,6-dicarboxylic acid 2-thiophen-2'-yl methyl ester following general procedure 5.

Yield (43%).

mp 226–228° C. $^1$H-NMR (DMSO-D$_6$-TFA-D, 200.15 MHz): 7.54 (dd, J=5.06, 1.16 Hz, 1H); 7.17 (d, J=2.50 Hz, 1H); 7.02 (dd, J=5.06, 3.48 Hz, 1H); 5.32 (s, 2H); 1.90–1.67 (m, 6H); 1.24–1.09 (m, 1H). $^{13}$C-NMR (DMSO-D$_6$-TFA-D, 50 MHz): 173.0, 170.2, 137.1, 129.2, 128.3, 127.4, 65.4, 62.6, 32.5, 30.3, 28.3, 26.8, 21.1.

EXAMPLE 51

(1S,2S,5R,6S)2-Amino-bicyclo[3.1.0]hexane-2,6-dicarboxylic acid 6-(3',5'-dichloro)benzyl ester

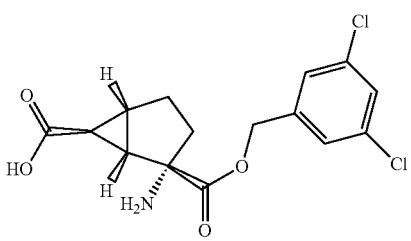

The title compound was prepared from 2-Allyloxycarbonylamino-bicyclo[3.1.0]hexane-2,6-dicarboxylic acid 6-(3',5'-dichloro)benzyl ester following general procedure 5. (yield 65%).

$^1$H-NMR (CD$_3$OD, 200.15 MHz): 7.56 (t, J=2 Hz, 1H); 7.45 (d, J=2 Hz, 2H); 5.14 (s, 2H); 2.07–1.70 (m, 6H); 1.29–1.09 (m, 1H). $^{13}$C-NMR (DMSO-D6, 50 MHz): 174.8, 174.0, 140.5, 134.1, 127.5, 126.1, 65.4, 64.3, 36.2, 33.1, 30.6, 27.9, 26.4, 20.5.

EXAMPLE 52

(1S,2S,5R,6S)-2-Amino-2-(2',3'-difluorobenzyloxycarbonyl)-bicyclo[3.1.0]hexane-6-dicarboxylic acid

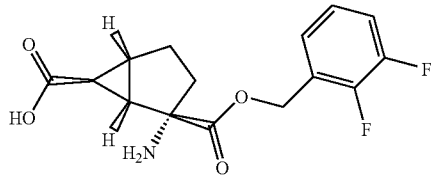

(1S,2S,5R,6S)-6-Allyl-2-(2',3'-difluorobenzyl)-2-allyloxycarbonylamino-bicyclo[3.1.0]hexane-2,6-dicarboxylate (685 mg, 1.6 mmol) was reacted with dimethylbarbituric acid (246 mg, 1.6 mmol) and tetrakistriphenylphosphine palladium (0) (36 mg; 0.02 mmol) following general procedure 5. The title compound was obtained as a white solid (340 mg, 70% yield).

mp 218–221° C.

$[\alpha]_D^{25}=-2°$ (c=1.1, HCl(1N)).

$^1$H NMR (Methanol-d$_4$) δ: 7.37–7.21 (m, 3H); 5.46 (s, 2H); 2.31–2.00 (m, 6H); 1.66–1.48 (m, 1H).

$^{13}$C NMR (Methanol-d$_4$+TFA-d) δ: 173.2, 169.6, 125.5, 124.5 (t, J=4.8 Hz), 117.7 (d, J=27.3 Hz), 65.6, 61.4, 32.3, 29.9, 28.4, 26.3, 20.8.

I.R. (KBr): 3443, 3252, 1736, 1724, 1541.

MS (Electrospray)M$^+$+1: 312.

EXAMPLE 53

(1S,2S,5R,6S)-2-Amino-2-(2'-butoxybenzyloxycarbonyl)-bicyclo[3.1.0]hexane-6-carboxylic acid

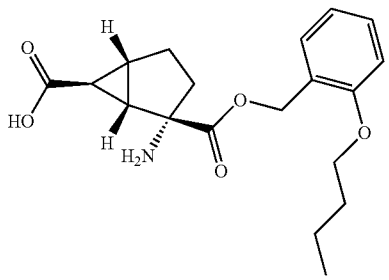

(1S,2S,5R,6S)-2-(2'-butoxy-benzyl)-6-allyl 2-allyloxycarbonylamino-bicyclo[3.1.0]hexane-2,6-dicarboxylate (1.2 mg, 2.5 mmol) was reacted with dimethylbarbituric acid (384 mg, 2.5 mmol) and tetrakistriphenylphosphine palladium (0) (57 mg; 0.05 mmol) following general procedure 5. The title compound was obtained as a white solid 500 mg, 58% yield).

mp 176–178° C.

$[\alpha]_D^{25}$=–7° (c=1, HCl(1N)).

$^1$H-NMR (DMSO-$d_6$+TFA-d) δ: 7.37–7.29 (m, 2H); 7.05–6.91 (m, 2H); 5.29 and 5.21 (AB system, J=12.3 Hz, 2H); 4.00 (t, J=6.4 Hz, 2H); 2.08–1.93 (m, 6H); 1.75–1.64 (m, 2H); 1.50–1.39 (m, 3H); 0.93 (t, J=7.3 Hz, 3H).

$^{13}$C-NMR (DMSO-$d_6$+TFA-d) δ: 173.5, 170.8, 157.6, 131.0, 130.5, 123.7, 121.0, 112.7, 68.3, 66.0, 64.3, 33.1, 31.6, 30.8, 28.8, 27.2, 21.6, 19.6, 14.5.

I.R. (KBr): 3445, 3250, 1734, 1722, 1543.

MS (Electrospray)M$^+$+1: 348.

EXAMPLE 54

(1S,2S,5R,6S)-2-Amino-bicyclo[3.1.0]hexane-2,6-dicarboxylic acid 2-(3'-fluoro)benzyl ester

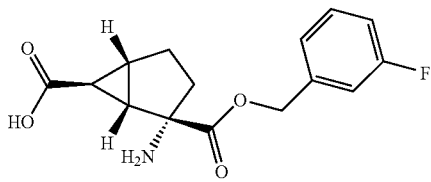

The tile compound was prepared following general procedure 5.

77% Yield. White solid. mp 225° C., dec.

$[\alpha]_D^{25}$=–2.40° (c=1.0, 1N HCl).

$^1$H NMR (D$_2$O/KOD) δ: 7.39–7.32 (m, 1H), 7.17–7.00 (m, 3H), 4.59 (brs, 2H), 1.95–1.72 (m, 5H), 1.46 (t, 1H, J=2.8 Hz), 1.12–1.06 (m, 1H).

$^{13}$C NMR (D$_2$O/KOD, 125 MHz) δ: 183.6, 182.7, 162.8 (d, $J_{C-F}$=241 Hz), 143.3 (d, $J_{C-F}$=6.9 Hz), 130.5 (d, $J_{C-F}$=8.4 Hz), 123.1 (d, $J_{C-F}$=2.2 Hz), 114.4 (d, $J_{C-F}$=21.0 Hz), 113.9 (d, $J_{C-F}$=21.5 Hz), 66.5, 63.3, 36.7, 34.5, 28.0, 27.0, 24.0.

EXAMPLE 55

(1S,2S,5R,6S)-2-Amino-bicyclo[3.1.0]hexane-2,6-dicarboxylic acid 2-(2',5'-difluoro)benzyl ester

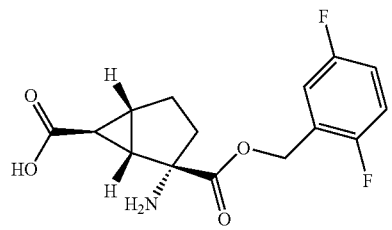

The tile compound was prepared using 0.5 equiv of BDMA following general procedure 5.

78% yield, White solid. mp: 193–196° C.

$^1$H NMR (CD$_3$OD) δ: 7.43–7.21 (m, 3H), 5.29 (s, 2H), 2.33–1.99 (m, 6H), 1.17 (m, 1H).

$^{13}$C NMR (CD$_3$OD) δ: 175.6, 172.0, 160.9 (d, 1C, $J_{C-F}$=242.0 Hz), 159.4 (d, 1C, $J_{C-F}$=244.0 Hz), 118.6–119.6 (4C), 68.0, 63.9, 34.7, 32.3, 30.7, 28.7, 23.2.

MS (Electrospray): 352, 303.

$[\alpha]_D^{25}$(1N HCl): –7.6°

EXAMPLE 56

(1S,2S,5R,6S)2-Amino-bicyclo[3.1.0]hexane-2,6-dicarboxylic acid 2-benzo[b]thiophen-2'-yl methyl ester

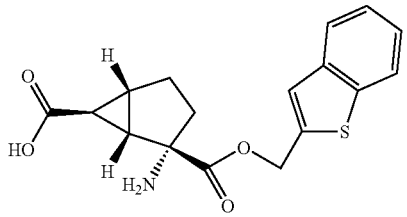

Prepared from 2-Allyloxycarbonylamino-bicyclo[3.1.0] hexane-2,6-dicarboxylic acid 6-allyl ester 2-benzo[b]thiophen-2'-yl methyl ester following general procedure 5. (63%). mp 234–234° C. $^1$H-NMR (DMSO-D$_6$-TFA-D, 200.15 MHz): 8.71 (br, 2H) 7.99–7.81 (m, 2H); 7.54 (s, 1H); 7.42–7.33 (m, 2H); 5.57 (s, 2H); 2.14–1.95 (m, 6H); 1.64–1.45 (m, 1H). $^{13}$C-NMR (DMSO-D$_6$-TFA-D, 50 MHz): 172.7, 169.8, 139.7, 138.8, 137.9, 125.0 (2×), 124.7, 124.0, 122.6, 65.1, 63.0, 32.2, 30.0, 28.0, 26.5, 20.8.

What is claimed is:

1. A compound of the formula I

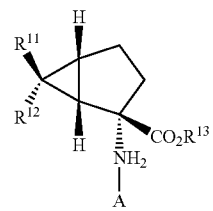

wherein
$R^{11}$ is $CO_2R^{14}$ and $R^{12}$ is hydrogen or fluoro; or $R^{11}$ is hydrogen or fluoro and $R^{12}$ is $CO_2R^{14}$;
$R^{13}$ and $R^{14}$ are, independently, hydrogen, (1–10C) alkyl, (2–4C) alkenyl, aryl or arylalkyl;
A is $(Q)_p$-;
p is any integer from 1–10; and
Q is independently selected, each time taken, from the group amino acyl;
provided that the compound is not one in which $R^{11}$ is $CO_2R^{14}$; $R^{12}$, $R^{13}$ and $R^{14}$ are hydrogen; p is 1; and Q is L-alanyl;
or a pharmaceutically acceptable salt thereof.

2. A compound of the formula I

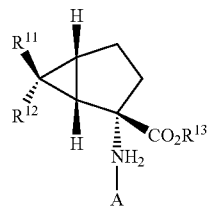

I wherein
$R^{11}$ is $CO_2R^{14}$ and $R^{12}$ is hydrogen or fluoro; or $R^{11}$ is hydrogen or fluoro and $R^{12}$ is $CO_2R^{14}$;
$R^{13}$ and $R^{14}$ are, independently, hydrogen, (1–10C) alkyl, (2–4C) alkenyl, aryl or arylalkyl;
A is $(Q)_p$-;
p is any integer from 1–10; and
Q is independently selected, each time taken, from the group amino acyl wherein amino acyl is an ?-amino acid;
provided that the compound is not one in which $R^{11}$ is $CO_2R^{14}$; $R^{12}$, $R^{13}$ and $R^{14}$ are hydrogen; p is 1; and Q is L-alanyl;
or a pharmaceutically acceptable salt thereof.

3. The compound (or salt thereof) of claim 1 or 2 wherein (1–10C) alkyl is methyl.

4. The compound (or salt thereof) of claim 1 or 2 wherein $R^{11}$ is $CO_2R^{14}$;
$R^{12}$, $R^{13}$, $R^{14}$ and $R^{15}$ are hydrogen; and
p is any integer from 1–3.

5. The compound (or salt thereof) of claim 1 or 2 wherein Q is independently selected, each time taken, from L-alanyl, glycyl, L-leucyl, L-phenylalanyl, L-valyl, L-lysyl, L-tryptophyl, L-isoleucyl, L-methionyl, L-glutamyl, L-tyrosyl, D-alanyl, L-prolyl, L-serinyl, D-leucyl, L-asparagyl and L-threonyl.

6. The compound which is selected from:
a) (1S,2S,5R,6S)-2-[(2'S)-(2'-Amino)-3'-phenylpropionyl]amino-bicyclo[3.1.0]hexane-2,6-dicarboxylic acid hydrochloride;
b) (1S,2S,5R,6S)-2-[(2'S)-(2'-Amino)-3'-methylbutyryl]amino-bicyclo[3.1.0]hexane-2,6-dicarboxylic acid hydrochloride;
c) (1S,2S,5R,6S)-2-[(2'S,3'S)-(2'-Amino-3'-methyl-pentanoylamino)-bicyclo[3.1.0]hexane-2,6-dicarboxylic acid hydrochloride;
d) (1S,2S,5R,6S)-2-(2-Amino-acetylamino)-bicyclo[3.1.0]hexane-2,6-dicarboxylic acid;
e) (1S,2S,5R,6S)-2-[(2'S)-(2'-Amino)-(4'-methylthio)-butyryl]amino-bicyclo[3.1.0]hexane-2,6-dicarboxylic acid;
f) (1S,2S,5R,6S)-2-[(2'S)-(2'-amino)-(3'-p-hydroxyphenyl)-propionyl]amino-bicyclo[3.1.0]hexane-2,6-dicarboxylic acid;
g) (1S,2S,5R,6S)-2-[(2'S,3'R)-2-amino-3-hydroxy)-butyryl)amino-bicyclo[3.1.0]hexane-2,6-dicarboxylic acid;
h) (1S,2S,5R,6S)-2-[2'S-(2"S-amino-4-methyl-pentanonylamino)-propionylamino]-bicyclo[3.1.0]hexane-2,6-dicarboxylic acid; or
i) (1S,2S,5R,6S)-2-[2'(S)-(2"(S)-amino-propionylamino)-propionylamino]-bicyclo[3.1.0]hexane-2,6-dicarboxylic acid.

7. A compound which is (1S,2S,5R,6S)-2-[(2'S)-(2'-amino-4'-methyl)-pentanoyl]amino-bicyclo[3.1.0]hexane-2,6-dicarboxylic acid.

8. A pharmaceutically acceptable salt of a compound of formula I as claimed in any one of claim 1 or 2 which is an acid-addition salt made with an acid which provides a pharmaceutically acceptable anion or, for a compound which contains an acidic moiety, which is a salt made with a base which provides a pharmaceutically acceptable anion.

9. The pharmaceutically acceptable salt of a compound of formula I as claimed in claim 8 wherein the salt is a hydrochloride salt.

10. The pharmaceutically acceptable salt of a compound of formula I as claimed in claim 8 wherein the salt is a methane sulfonate salt.

11. A pharmaceutical formulation comprising in association with a pharmaceutically acceptable carrier, diluent or excipient, a compound of formula I (or a pharmaceutically acceptable salt thereof) as provided claim 1 or 2.

12. A compound of formula IV

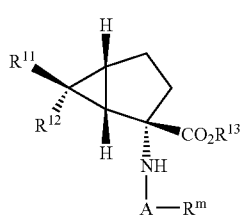

IV wherein $R^m$ is an amine protecting group and the groups $R^{11}$, $R^{12}$ and $R^{13}$ have any of the values defined in claim 1.

* * * * *